US008802193B2

(12) United States Patent
Gazit et al.

(10) Patent No.: US 8,802,193 B2
(45) Date of Patent: Aug. 12, 2014

(54) VAPOR DEPOSITION OF BIOMOLECULES

(75) Inventors: Ehud Gazit, Ramat-HaSharon (IL); Lihi Adler-Abramovich, Rishon-LeZion (IL); Daniel Aronov, Kfar-Yona (IL); Gil Rosenman, Rishon-LeZion (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 917 days.

(21) Appl. No.: 12/678,168

(22) PCT Filed: Aug. 13, 2008

(86) PCT No.: PCT/IL2008/001118
§ 371 (c)(1),
(2), (4) Date: Mar. 15, 2010

(87) PCT Pub. No.: WO2009/034566
PCT Pub. Date: Mar. 19, 2009

(65) Prior Publication Data

US 2010/0204443 A1 Aug. 12, 2010

Related U.S. Application Data

(60) Provisional application No. 60/960,066, filed on Sep. 13, 2007, provisional application No. 61/064,044, filed on Feb. 12, 2008.

(51) Int. Cl.
*C23C 16/00* (2006.01)
*C23C 16/04* (2006.01)
*C07K 5/06* (2006.01)
*A61K 38/05* (2006.01)

(52) U.S. Cl.

CPC ............... *C23C 16/00* (2013.01); *C23C 16/042* (2013.01); *A61K 38/05* (2013.01); *C07K 5/06* (2013.01)

USPC .................... 427/255.28; 427/585; 514/21.91

(58) Field of Classification Search
CPC ...... C23C 14/00; C23C 16/00; C23C 16/042; A61K 38/05; C07K 5/06

USPC ........................... 427/585, 255.28; 514/21.91

See application file for complete search history.

(56) References Cited

U.S. PATENT DOCUMENTS

| | | | | |
|---|---|---|---|---|
| 6,613,755 | B2 * | 9/2003 | Peterson et al. | ................ 514/63 |
| 7,238,389 | B2 | 7/2007 | Long et al. | |
| 2003/0015140 | A1 | 1/2003 | Van Slyke et al. | |

FOREIGN PATENT DOCUMENTS

| | | |
|---|---|---|
| EP | 0632143 | 1/1995 |
| WO | WO 2009/034566 | 3/2009 |

OTHER PUBLICATIONS

Benvenuti et al., Nature Protocols, 2007, 2(7):1633-1651.*
Kühnle et al. (J. Amer. Chem. Soc., 2003, 125:14680-14681).*
Zhang et al. (App. Phys. Let., 2001, 79:3155-3157).*
Huang et al. (Appl. Phys. Let., 2003, 82:460-462).*
Colomer et al. (Chem. Phys. Let., 2000, 317:83-89).*
Hayashi et al. (Langmuir, 2002, 18:7469-7472).*
Thissen et al. (Smart Mater. Struct., 2002, 11:792-799).*

(Continued)

*Primary Examiner* — Christopher M Babic
*Assistant Examiner* — Jeremy C Flinders

(57) ABSTRACT

A coating method is disclosed. The coating method comprises placing a substrate and a biomolecule in a chamber and applying a vapor deposition process within the chamber so as to form a solid deposition of the biomolecule on at least a portion of a surface of the substrate.

11 Claims, 24 Drawing Sheets
(21 of 24 Drawing Sheet(s) Filed in Color)

(56) References Cited

OTHER PUBLICATIONS

Communication Relating to the Results of the Partial International Search Dated Dec. 1, 2008 From the International Searching Authority Re.: Application No. PCT/IL2008/001118.

International Preliminary Report on Patentability Dated Mar. 25, 2010 From the International Bureau of WIPO Re.: Application No. PCT/IL2008/001118.

international Search Report Dated Feb. 20, 2009 From the international Searching Authority Re.: Application No. PCT/IL2008/001118.

Written Opinion Dated Feb. 20, 2009 From the International Searching Authority Re.: Application No. PCT/IL2008/001118.

Dubois et al. "Synthesis, Structure, and Properties of Model Organic Surfaces", Annual Reviews, XP002513254, 43: 437-463, 1992. p. 441, Lines 6-8.

Vaidya et al. "Computer-Controlled Laser Ablation: A Convenient and Versatile Tool for Micropatterning Biofunctional Synthetic Surfaces for Applications in Biosensing and Tissue Engineering", Biotechnology Progress, XP000852569, 14(3): 371-377, Jan. 1, 1998. p. 371, r-h Col., Lines 1-27, Fig.4.

Communication Pursuant to Article 94(3) EPC Dated Mar. 8, 2013 From the European Patent Office Re. Application No. 08789792.2.

* cited by examiner

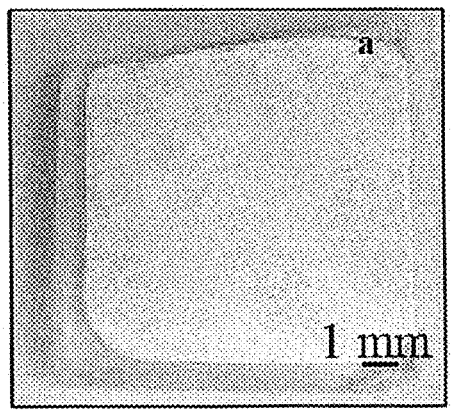
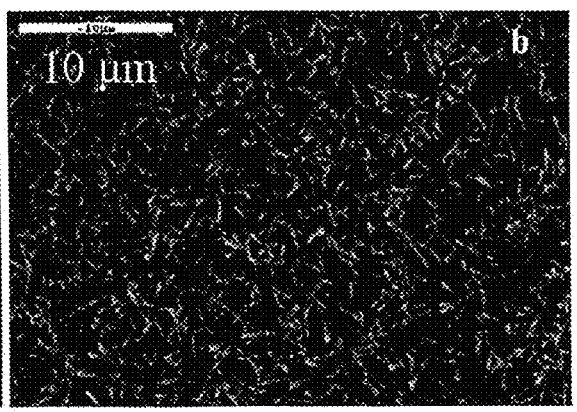
FIG. 2A    FIG. 2B
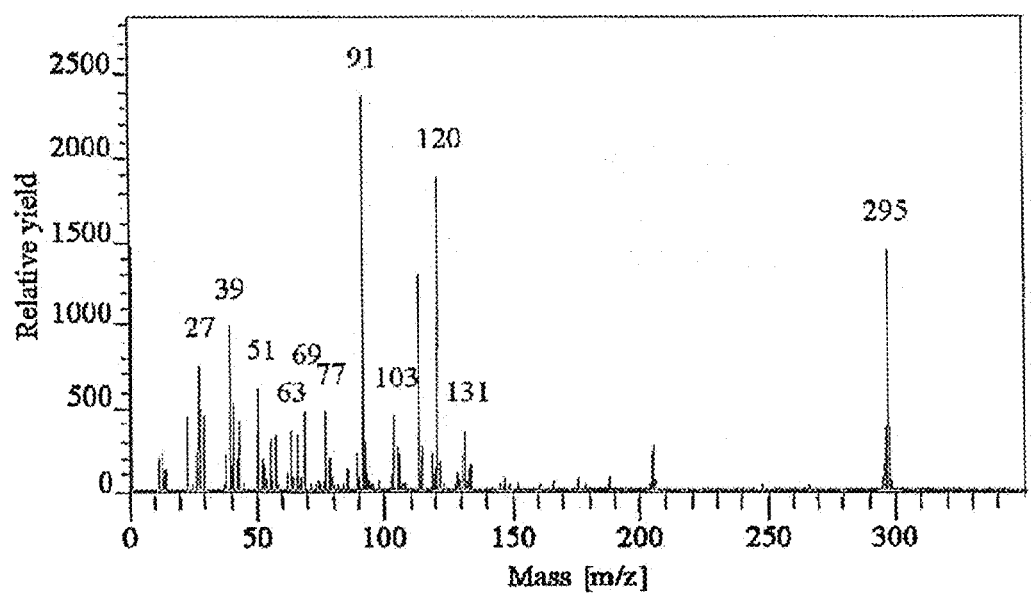
FIG. 3

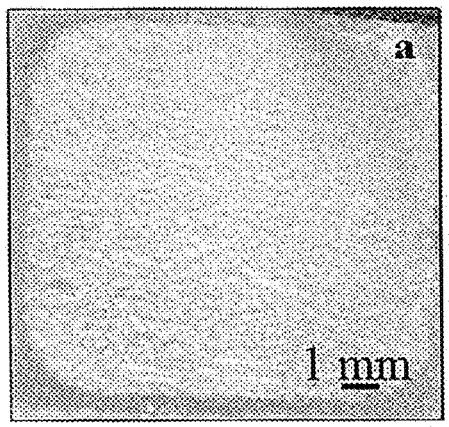
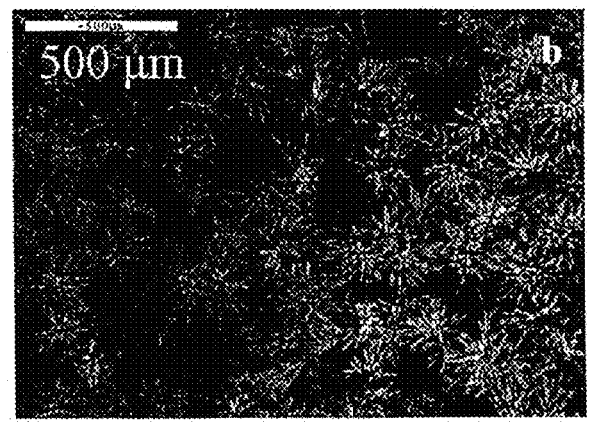
FIG. 8A	Fig. 8B
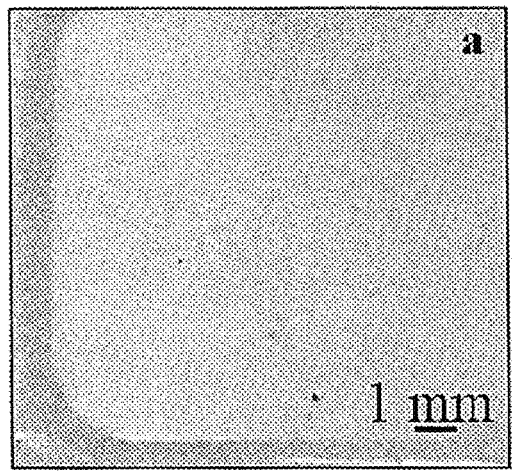
FIG. 9

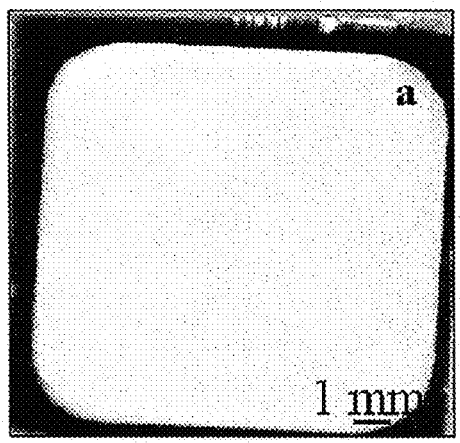
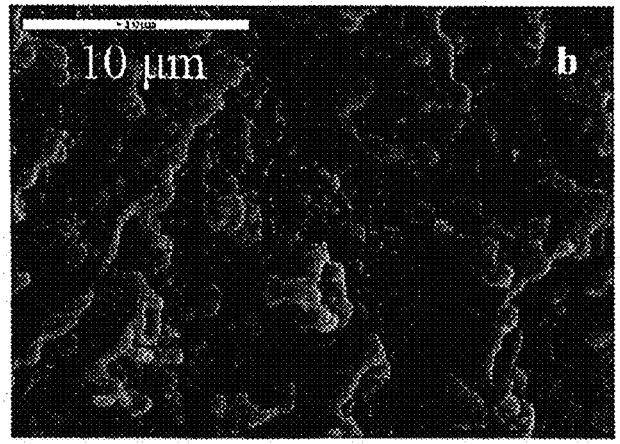
FIG. 10A  FIG. 10B
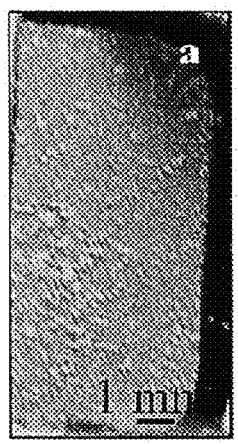
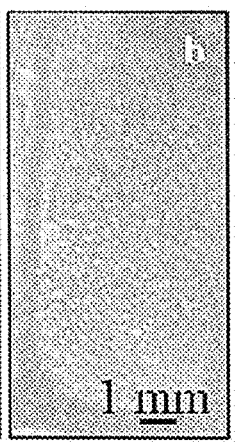
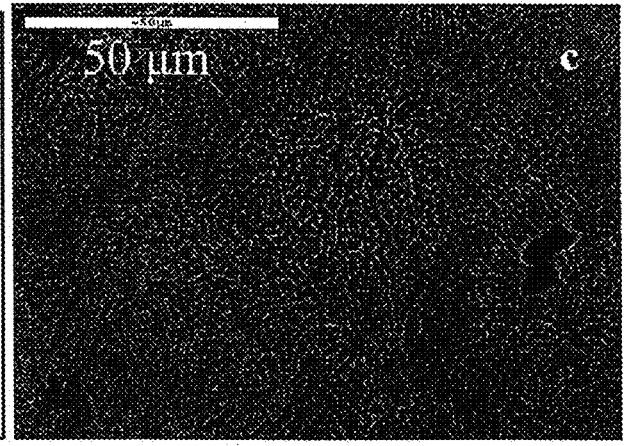
FIG. 11A  FIG. 11B  FIG. 11C FIG. 12A
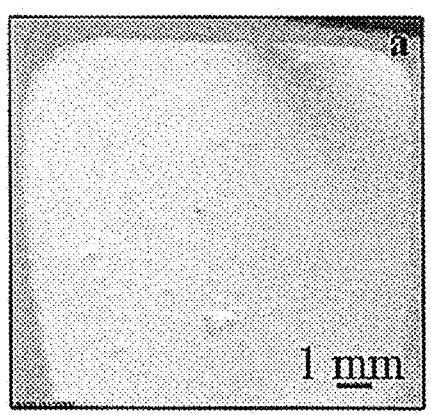
FIG. 12B
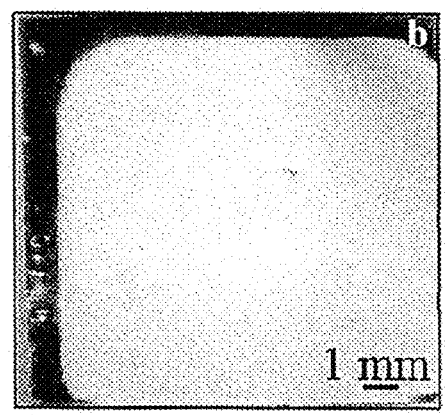
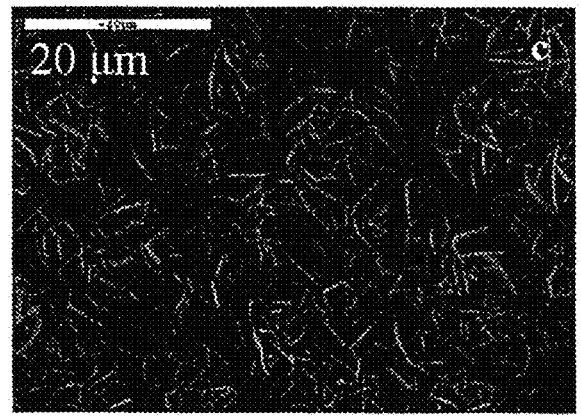
FIG. 12C FIG. 13A
FIG. 13B
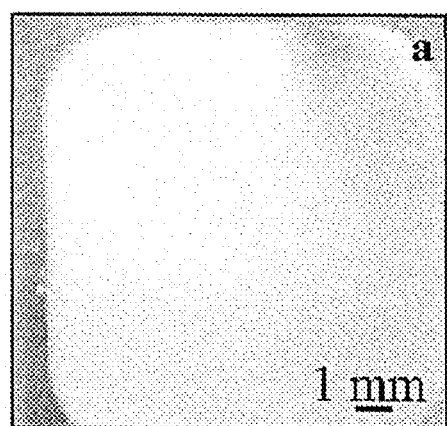
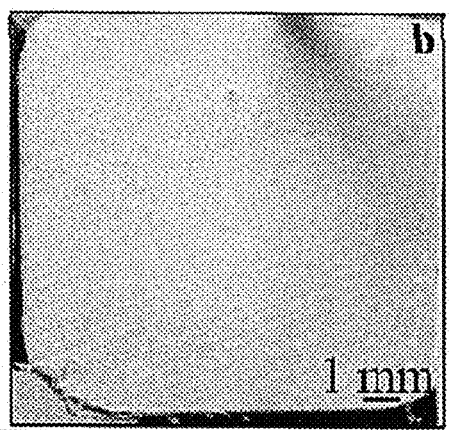
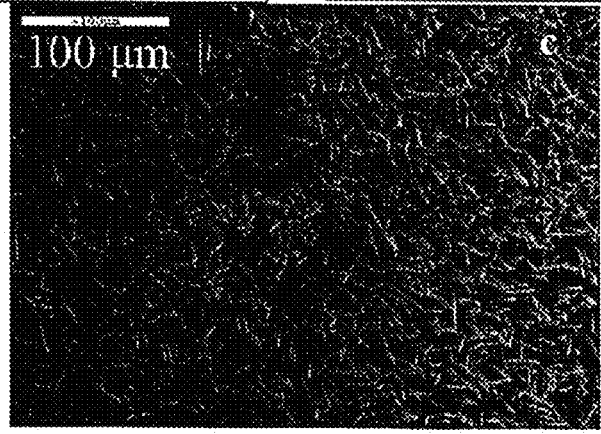
FIG. 13C

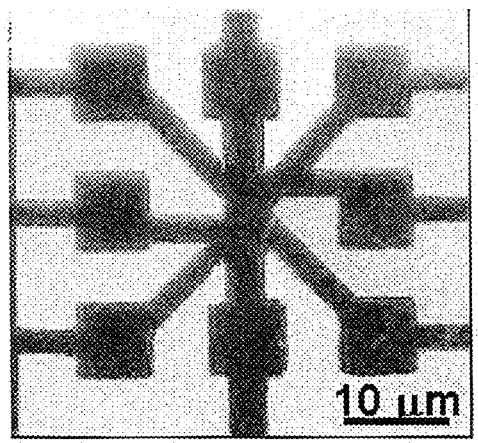 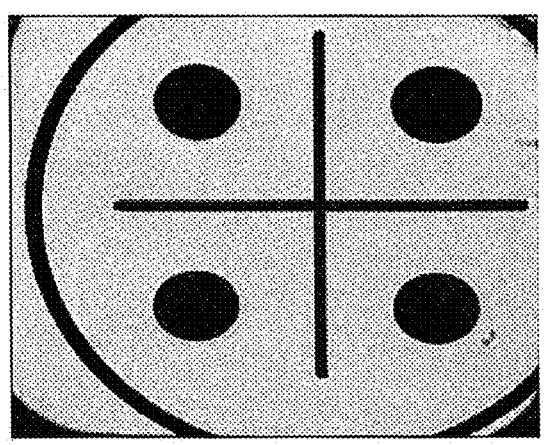
FIG. 31A  FIG. 31B
FIG. 32 ized form
VAPOR DEPOSITION OF BIOMOLECULES

RELATED APPLICATIONS

This Application is a National Phase of PCT Patent Application No. PCT/IL2008/001118 having International filing date of Aug. 13, 2008, which claims the benefit of U.S. Provisional Patent Application Nos. 61/064,044 filed on Feb. 12, 2008, and 60/960,066 filed on Sep. 13, 2007. The contents of the above Applications are all incorporated herein by reference.

FIELD AND BACKGROUND OF THE INVENTION

The present invention, in some embodiments thereof, relates to applied materials and more particularly, but not exclusively, to vapor deposition techniques utilizing biomolecules such as peptides, and applications thereof.

Vapor deposition is a general term used to describe any of a variety of methods for depositing a thin film of a material by the condensation, reaction or conversion of a vaporized form of the material, or a precursor thereof, onto the surface of various substrates. Thin films are thin material layers ranging from fractions of a nanometer to several micrometers in thickness. Vapor deposition is used to form a coat (film) of the deposited material so as to alter the mechanical (such as wear properties, lubrication and friction), electrical (such as semi-conductivity), electrochemical (such as electrode efficiency), thermal (such as heat conductivity), optical (such as light reflectivity), chemical (such as corrosion resistance, chemical compatibility, wettability and hydrophobicity), biological (such as anti-microbial and cells adhesion) of the substrates. Vapor deposition is also used to form free-standing bodies, wherein the substrate support is removed, such as films and fibers and composite materials.

Vapor deposition processes typically belong to one of two categories of vapor deposition processes: physical vapor deposition (PVD) and/or chemical vapor deposition (CVD), both of which are usually performed in a vacuum chamber.

In PVD, the coating method involves mainly physical processes such as, for example, elevated temperatures, high vacuum or plasma sputter bombardment, rather than a chemical reaction of a vaporized material at the surface to be coated, as in chemical vapor deposition (CVD). Evaporative deposition is a PVD process in which the material to be deposited is heated to a high vapor pressure by electrically resistive heating in "high" vacuum. Electron beam deposition is a PVD process in which the material to be deposited is heated to a high vapor pressure by electron bombardment in "high" vacuum. Sputter deposition is a PVD process in which a glow plasma discharge (usually localized around the "target" by a magnet) bombards the material sputtering some of it away as a vapor. Cathodic arc deposition is a PVD process in which a high power arc is directed at a material blasts some of it away into a vapor. Pulsed laser deposition is a PVD process in which a high power laser ablates material into a vapor.

PVD methods produce even and homogeneous coating of entire objects in a relatively straight-forward procedure, however, the physical conditions to which the subject and the coating material are subjected-to are rather harsh, and therefore may harm some heat sensitive target materials.

SUMMARY OF THE INVENTION

Some embodiments of the present invention relate a vapor, gas or aerosol of biomolecules such as, but not limited to, amino acids, polypeptides of various lengths, dipeptides, proteins, carbohydrates, saccharides and polysaccharides of various lengths, nucleotides and nucleic acids of various lengths, lipids, hormones, vitamins, antibiotics and other bioactive agents.

Some embodiments of the present invention relate to a technique for vapor deposition of biomolecules.

Vapor deposition is a widely used technique for coating surfaces of solid objects with various substances, whereby high vacuum and elevated temperatures are employed to vaporize the substance and allow it to deposit on the surface of the object. Despite its advanced and widespread use, vapor deposition has not been employed hitherto to coat objects with biomolecules, particularly since many biomolecules, such as peptides and proteins, are sensitive to the physical conditions employed during the process.

The present embodiments contemplate many types of biomolecules to be deposited via the vapor deposition. Representative examples include, without limitation, amino acids, polypeptides of various lengths, carbohydrates, saccharides and polysaccharides of various lengths, nucleotides and nucleic acids of various lengths, lipids, hormones, vitamins, antibiotics and other bioactive agents.

Some embodiments of the present invention relate to substrates coated by a layer of biomolecules and uses thereof in medical devices such as implants and surgery tools, diagnostic devices such as biosensors, filtering devices and the likes. Some embodiments of the present invention relate to objects consisting essentially of a biomolecule, which objects have various shapes and forms such as, but not limited to, tapes, films, flakes, fibers, wires, needles, rods, spheres, tubes and the like.

In some embodiments of the present invention, the vapor deposition of a biomolecule onto a surface of a substrate is effected by placing the substrate and a sample of the biomolecule in a vacuum chamber, generating vacuum condition and subsequently heating the sample of the biomolecule in order to vaporize the biomolecule and deposit it onto the substrate.

According to some embodiments, the biomolecular deposit can take a variety of forms and shapes, such as a film, a needle, a rod, a fiber, a wire, a flake, a tube and an amorphous blob. According to some embodiments of the present invention the biomolecular deposit can be detached from the solid substrate to provide an object made from biomolecules and devoid of solid substrate.

According to some embodiments of the present invention, the coating film of biomolecule can be manipulated and modified for example, using masks, etching and other lithographic techniques so as to provide a pre-designed pattern.

According to an aspect of some embodiments of the present invention there is provided a coating method, which comprises placing a substrate and a biomolecule in a chamber and applying a vapor deposition process within the chamber so as to form a solid deposition of the biomolecule on at least a portion of a surface of the substrate.

According to some embodiments of the invention at least one of the substrate and the biomolecule is selected such that the biomolecule is self-assembled into nanostructures within the chamber during the vapor deposition process. Thus, according to some embodiments the solid deposition comprises nanostructures.

According to some embodiments of the invention the method further comprises, prior to the application of the vapor deposition process, placing a mask on the surface such that the solid deposition is formed at a predetermined pattern which comprises a plurality of distinct addressable locations.

According to some embodiments of the invention the method further comprises, subsequently to the application of the vapor deposition process placing a mask having a predetermined pattern which comprises a plurality of distinct addressable locations on the solid deposition, and irradiating the mask and the solid deposition such that the solid deposition is substantially degraded according to the pattern.

According to some embodiments of the invention the method further comprises the nanostructures are responsive to a force field and the method further comprises applying a force field during or subsequently to said application of said vapor deposition process so as to align said nanostructures generally parallel to each other.

According to some embodiments of the invention the method further comprises placing in the chamber a material which is responsive to a force field, and applying a force field during or subsequently to the application of the vapor deposition process so as to align the nanostructures generally parallel to each other.

According to some embodiments of the invention the method further comprising detaching the solid deposition from the surface, thereby obtaining the article-of-manufacture.

According to an aspect of some embodiments of the present invention there is provided a composition-of-matter which comprises a solid substrate and at least one type of a biomolecule deposited on a surface of the substrate by vapor deposition at a predetermined pattern which comprises a plurality of distinct addressable locations.

According to some embodiments of the invention the at least one type of biomolecule forms nanostructures along the pattern.

According to some embodiments of the invention a gap between any two adjacent locations of the plurality of locations ranges is at least 100 nm.

According to an aspect of some embodiments of the present invention there is provided a composition-of-matter which comprises a biomolecule and a solid substrate having thereon a solid deposition of the biomolecule deposited by vapor deposition and occupying at least a portion of a surface of the substrate.

According to an aspect of some embodiments of the present invention there is provided a composition-of-matter which comprises a peptide and a substrate having thereon a solid deposition of the peptide deposited by vapor deposition and occupying at least a portion of a surface of the substrate.

According to an aspect of some embodiments of the present invention there is provided an article-of-manufacture which comprises a solid deposition of a biomolecule, being formed by vapor deposition and devoid of any solid substrate attached thereto.

According to an aspect of some embodiments of the present invention there is provided an article-of-manufacture which comprises a solid deposition of a peptide, being formed by vapor deposition and devoid of any solid substrate attached thereto.

According to some embodiments of the invention vapor deposition process is a physical vapor deposition process.

According to some embodiments of the invention vapor deposition process is a chemical vapor deposition process.

According to some embodiments of the invention the biomolecule is selected from the group consisting of a peptide, a nucleic acid, a nucleotide and an amino acid.

According to some embodiments of the invention the solid deposition is characterized by a thickness ranging from about 100 nm to about 10 μm.

According to an aspect of some embodiments of the present invention there is provided a medical device comprising the composition described herein.

According to some embodiments of the invention the medical device is adapted for implantation in a subject.

According to an aspect of some embodiments of the present invention there is provided a sensor device comprising the composition described herein.

According to an aspect of some embodiments of the present invention there is provided an electrical energy storage device comprising the composition described herein.

According to an aspect of some embodiments of the present invention there is provided a self-cleaning surface comprising the composition described herein.

According to an aspect of some embodiments of the present invention there is provided a microfluidic device comprising the composition described herein.

As used herein the term "about" refers to ±10%.

The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a biomolecule" or "at least one biomolecule" may include a plurality of biomolecules, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

Figure 1A:
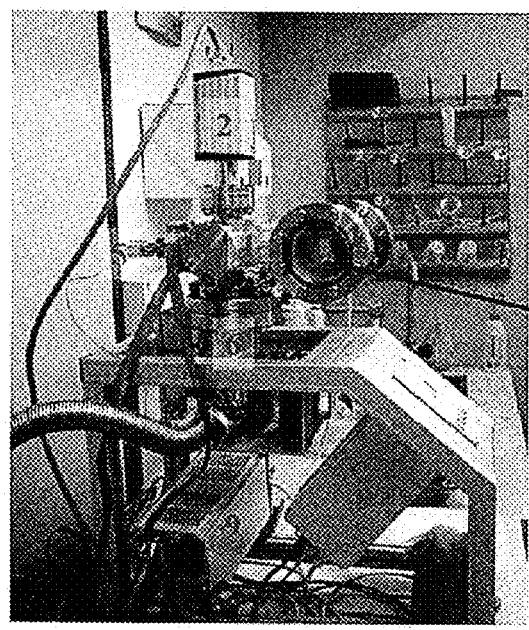
Figure 1B:
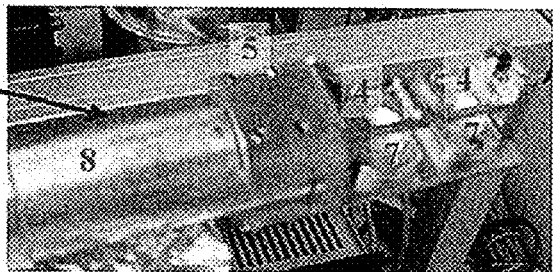
Figure 4A:
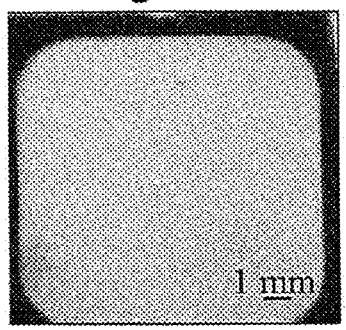
Figure 4C:
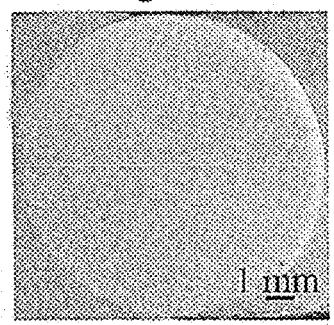
Figure 4E:
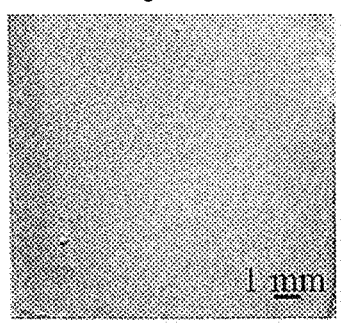
Figure 4B:
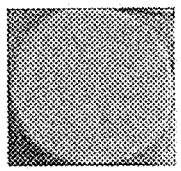
Figure 4D:
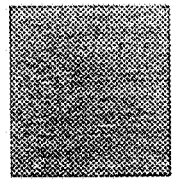
Figure 5B:
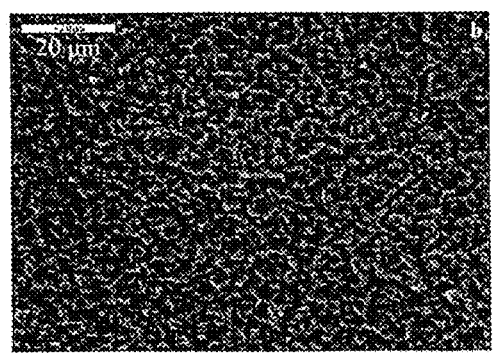
Figure 5A:
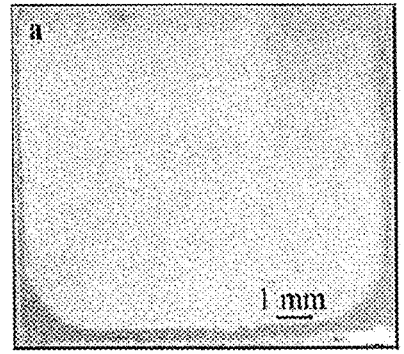
Figure 6:
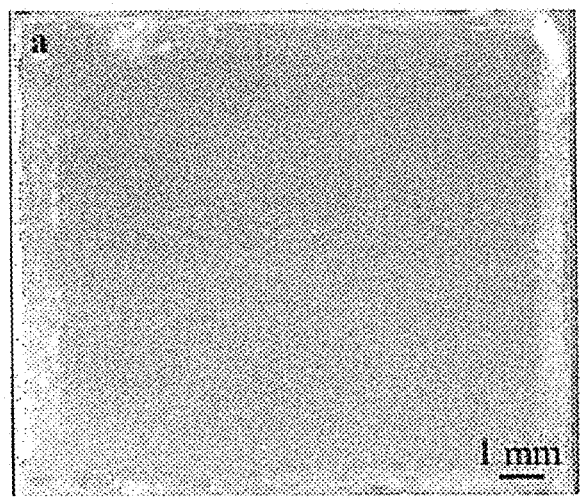
Figure 7A:
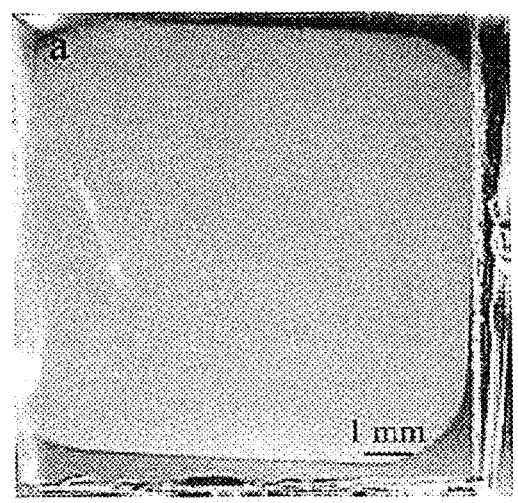
Figure 7B:
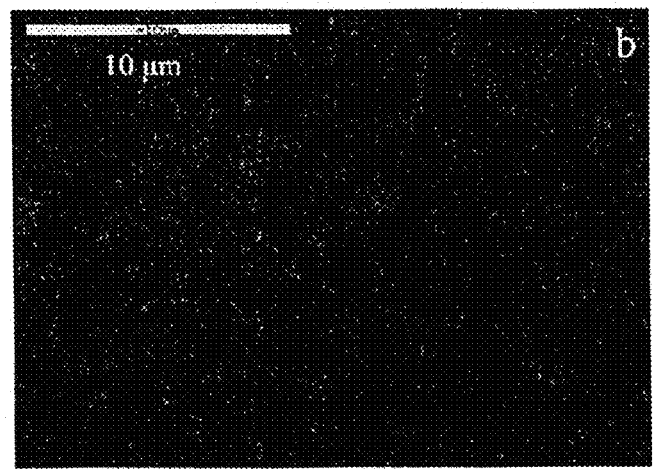
Figure 14:
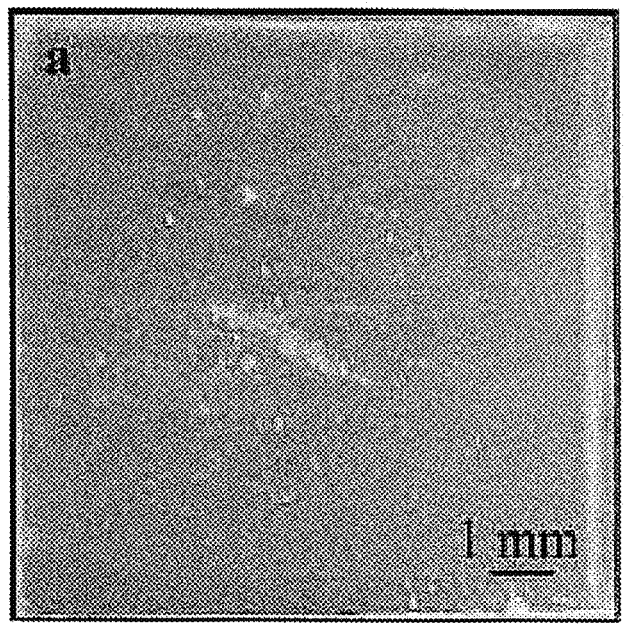
Figure 15:
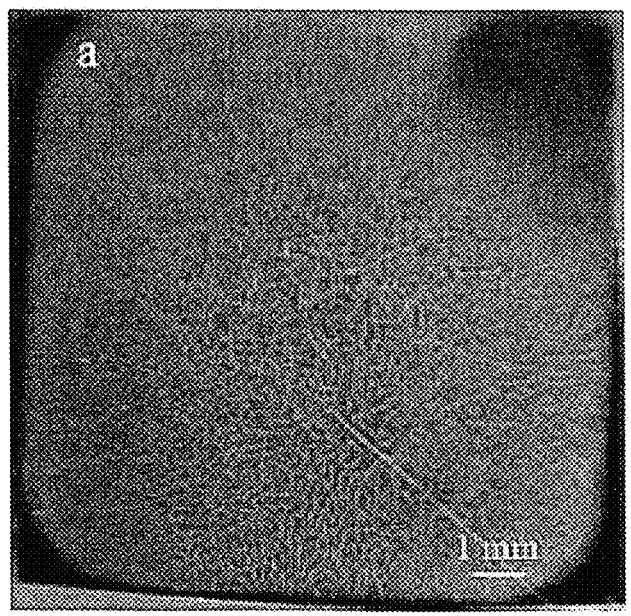
Figure 16:
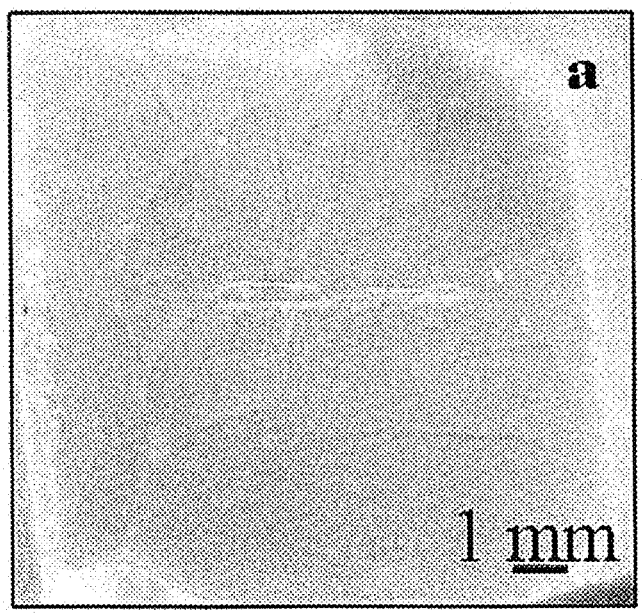
Figure 17:
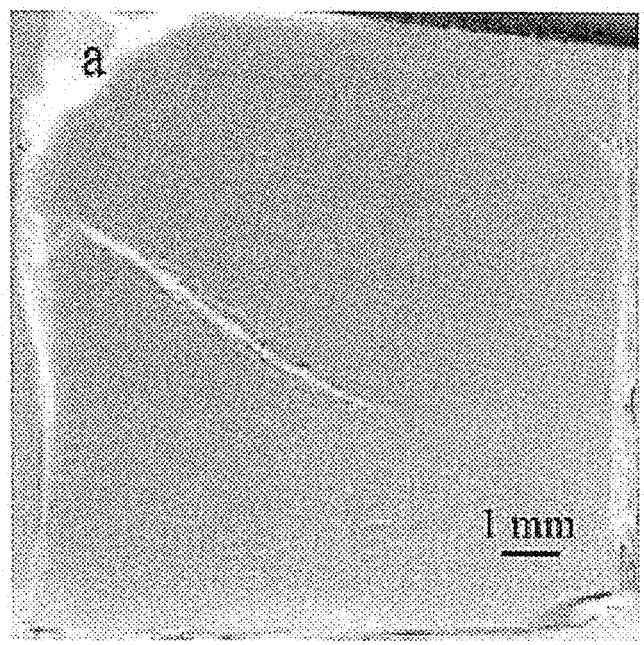
Figure 18:
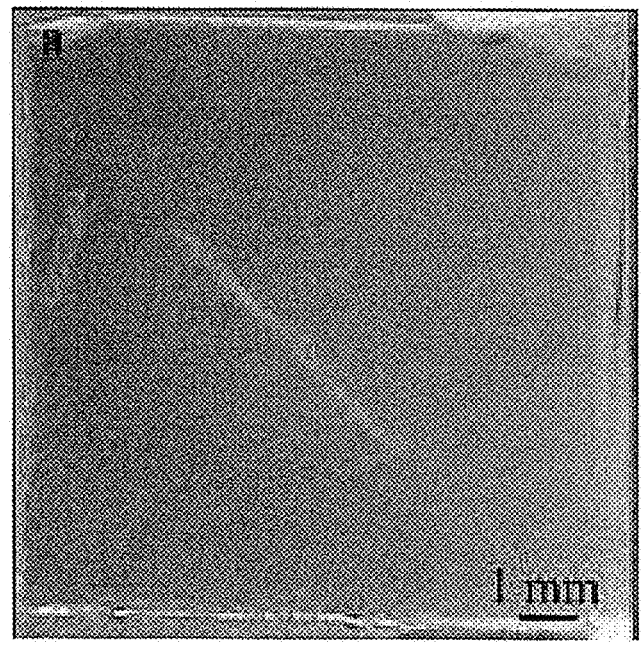
Figure 19:
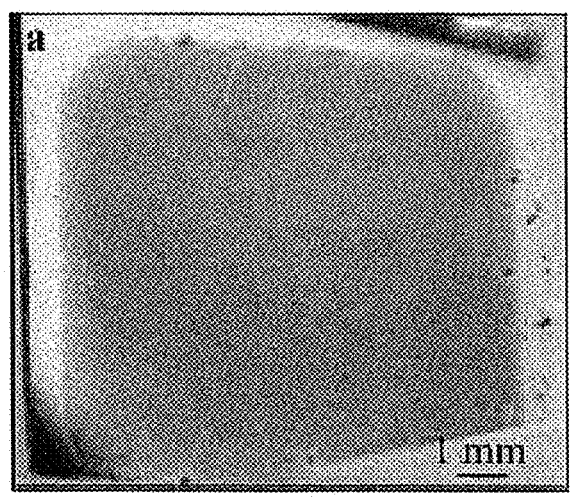
Figure 20A:
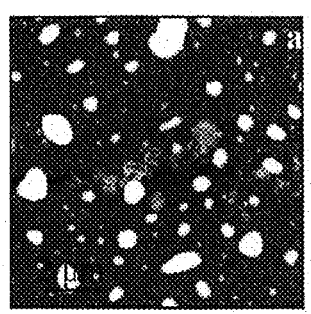
Figure 20B:
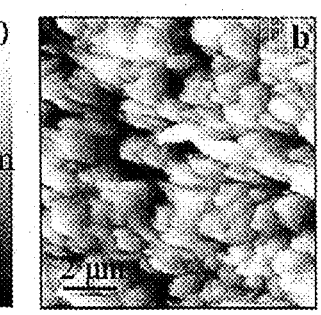
Figure 20C:
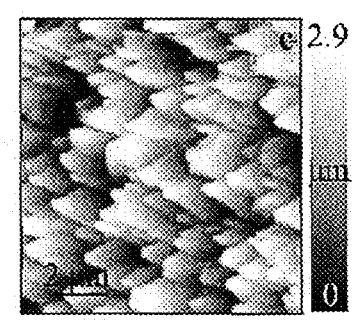
Figures 21A, 21B:
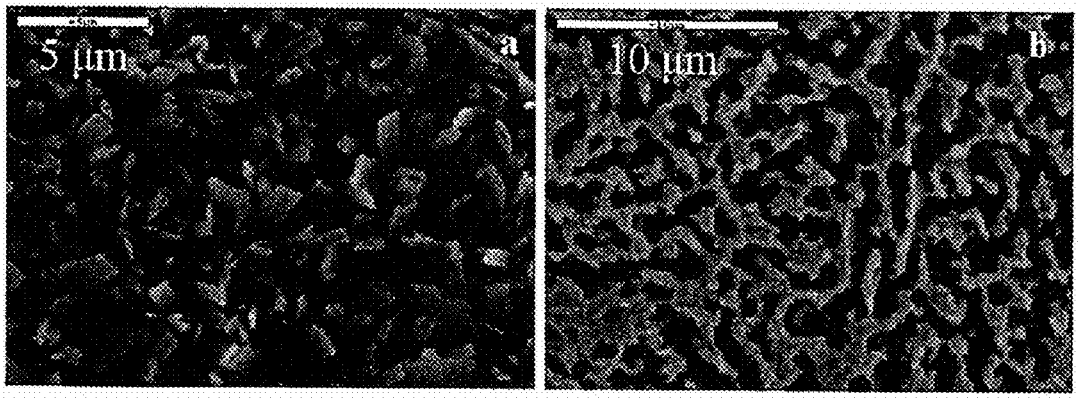
Figures 22A, 22B:
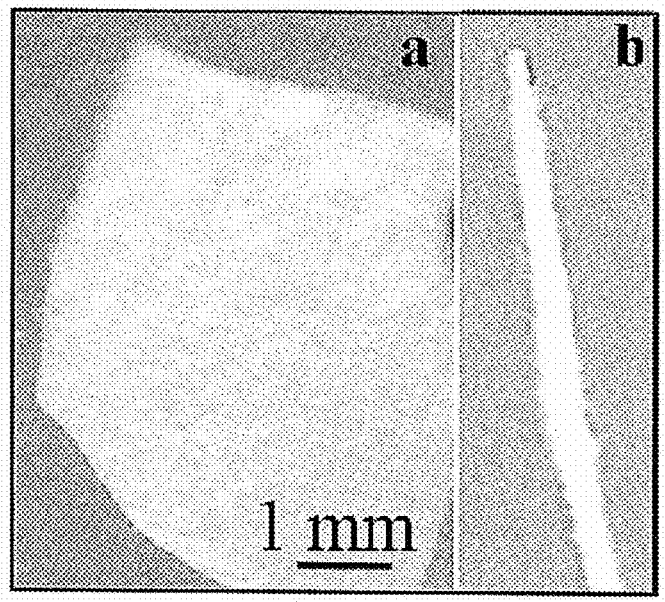
Figure 23:
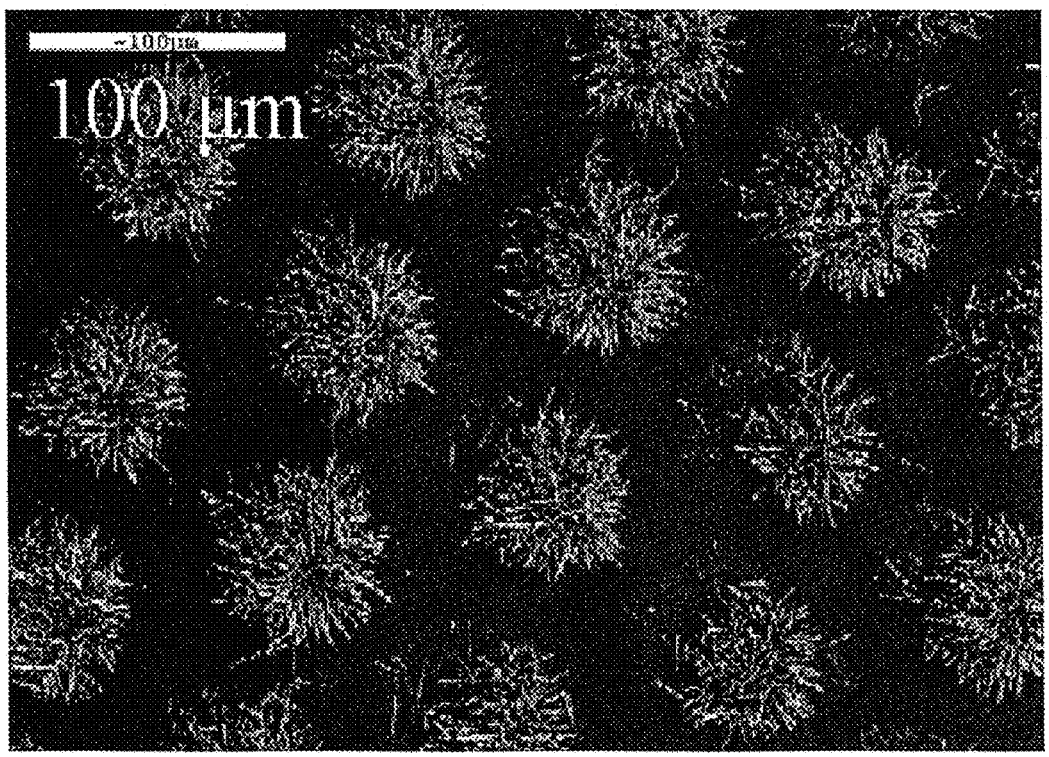
Figure 24:
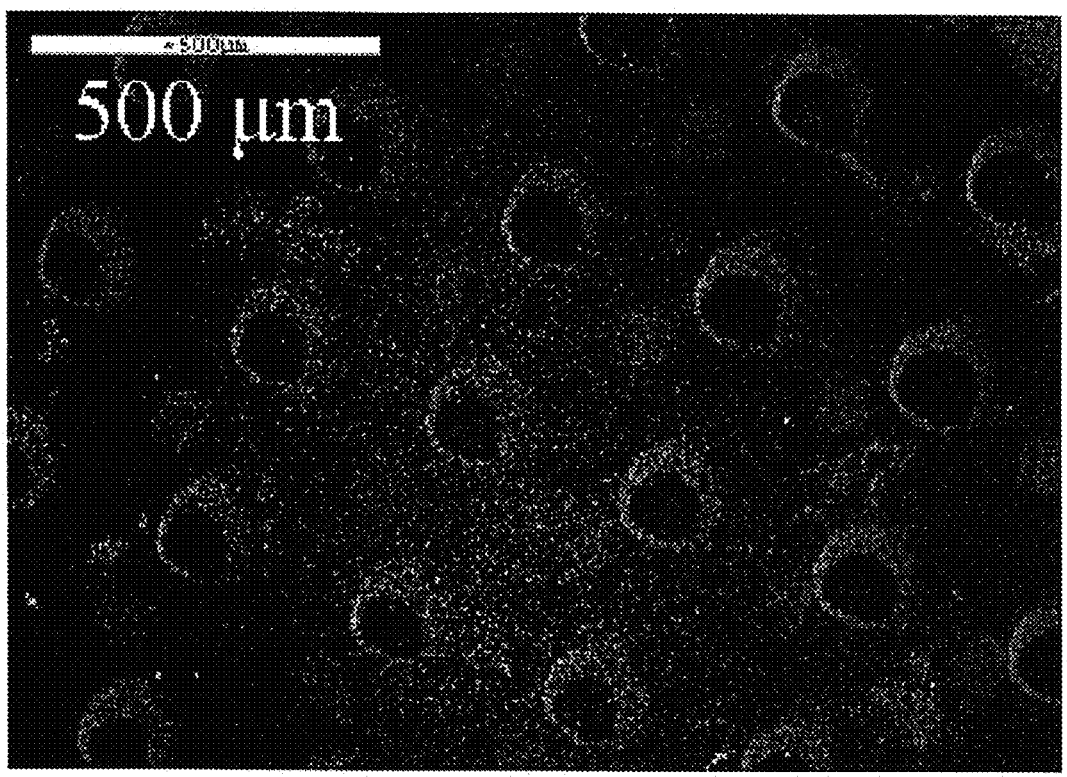
Figure 25A:
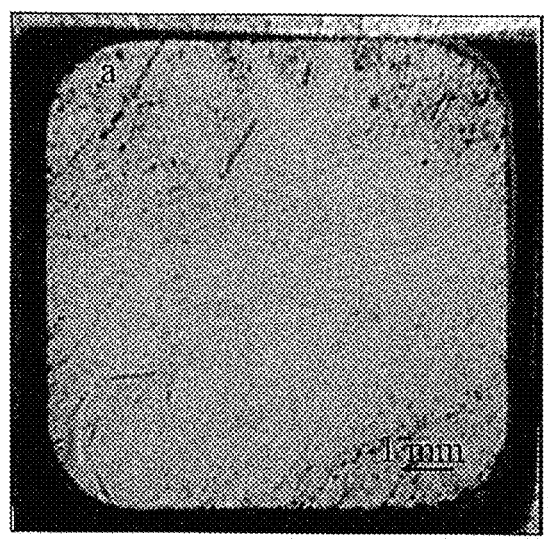
Figure 25B:
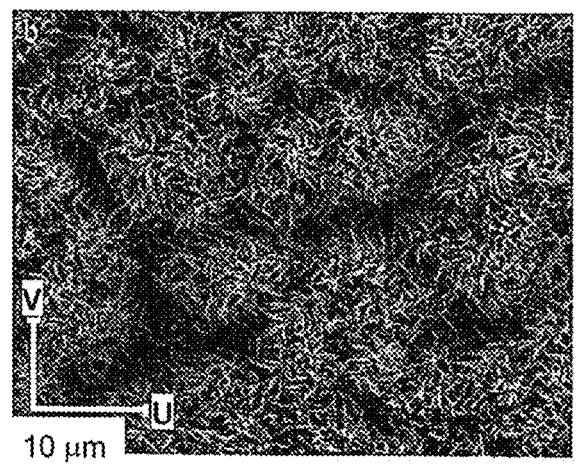
Figure 26:
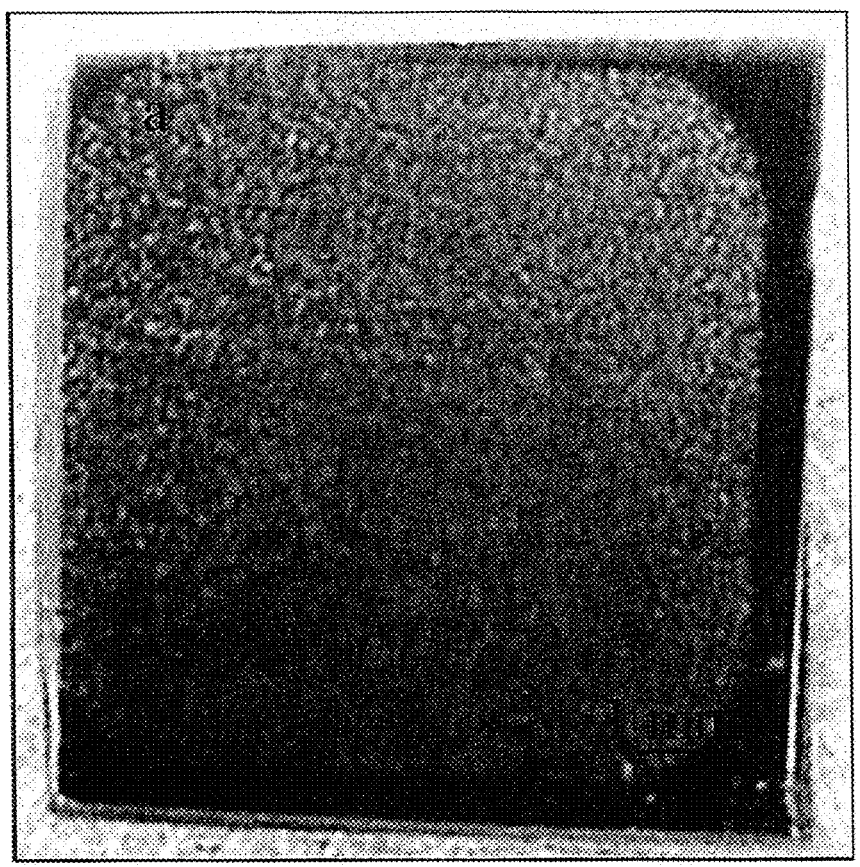
Figure 27:
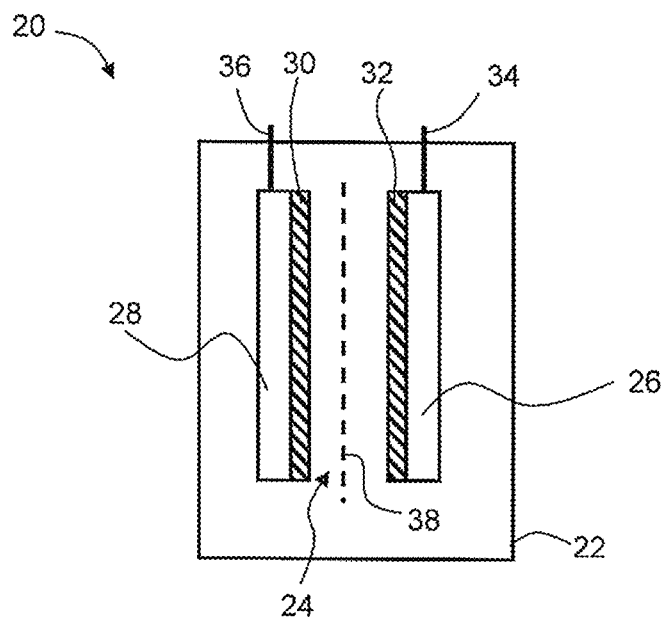
Figure 28:
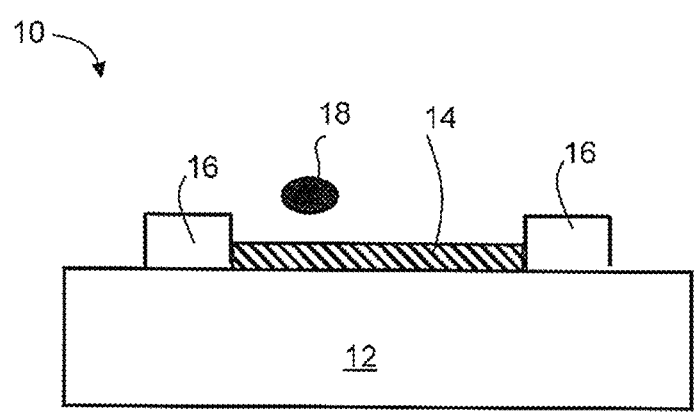
Figure 29:
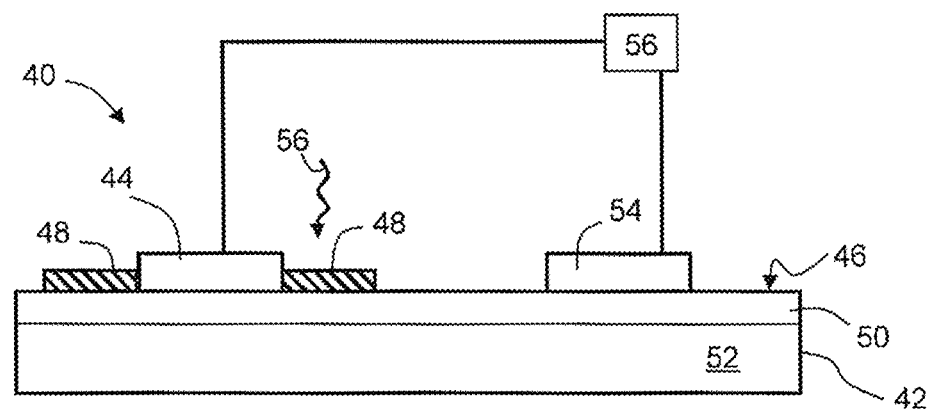
Figure 33A:
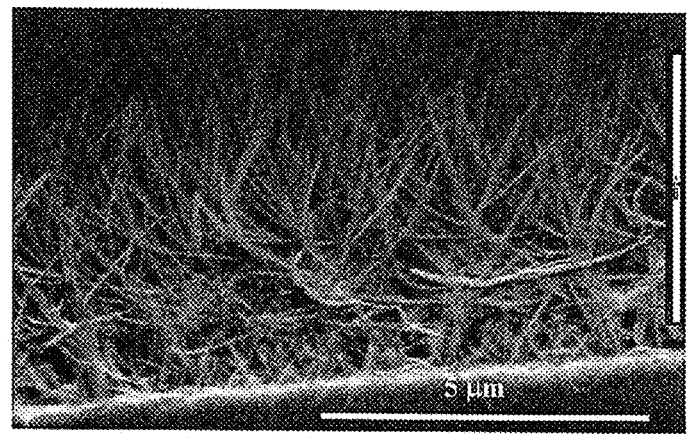
Figure 33B:
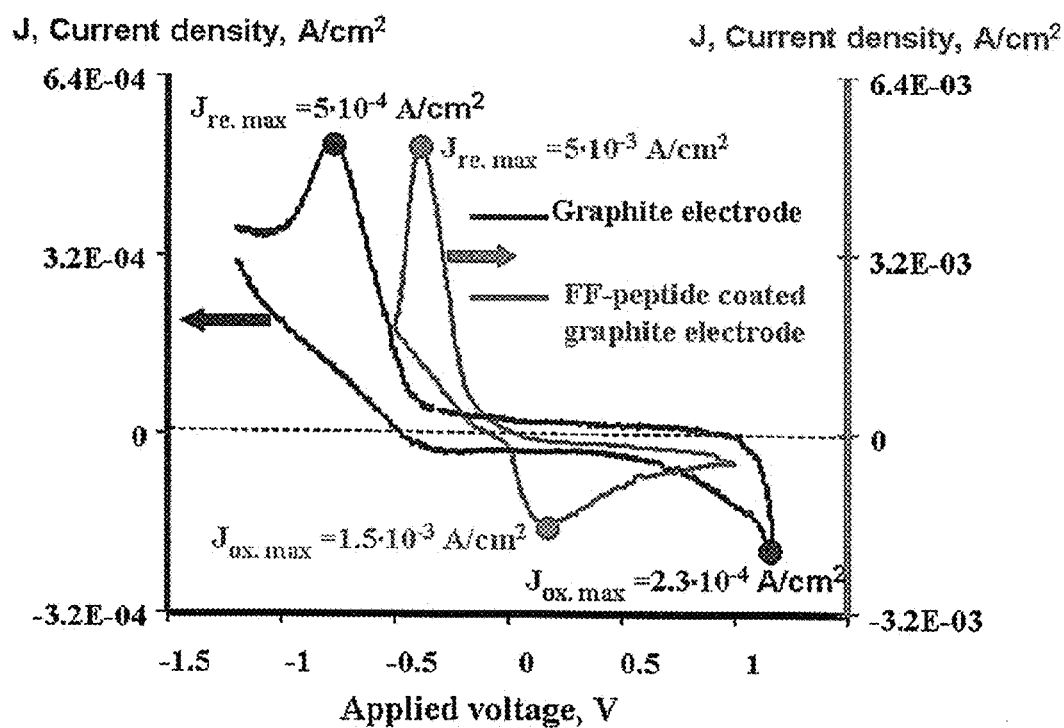

FIGS. 1A-B are images of an exemplary experimental setup for vapor deposition of biomolecules, used according to some embodiments of the present invention;

FIGS. 2A-B are images of a glass substrate having a film of diphenylalanine (FF) deposited thereon using a vapor deposition method according to embodiments of the present invention. FIG. 2A is a low magnification optical micrograph showing the uniform and homogeneous distribution of the FF film on the glass surface, and FIG. 2B is a high magnification SEM micrograph showing the needle-like microstructure of the deposited FF film on the glass surface;

FIG. 3 is a time-of-flight secondary-ion mass spectrogram obtained from a film of FF deposited on glass, showing the positive ions fingerprint of the vapor deposited FF having a peak at about 295 m/z, characteristic to FF;

FIGS. 4A-E are optical micrographs of the surfaces of different substrates onto which FF was deposited by a vapor deposition method according to some embodiments of the present invention, such as silicon dioxide (silica, $SiO_2$, FIG. 4A), hydroxylapatite ($Ca_5(PO_4)_3(OH)$, HAp) ceramics (FIG. 4B before deposition and FIG. 4C after deposition), and titanium (Ti, FIG. 4D before deposition and FIG. 4E after deposition);

FIGS. 5A-B are images of a glass substrate having a film of N-tert-butoxycarbonyl-diphenylalanine (Boc-FF) deposited thereon using a vapor deposition method of an embodiment of the present invention. FIG. 5A is a low magnification optical micrograph showing the uniform and homogeneous distribution of the Boc-FF film on the glass surface, and FIG. 5B is a high magnification SEM micrograph showing the scale-like microstructure of the deposited thin Boc-FF film on the glass surface;

FIG. 6 is a low magnification optical micrograph of a glass substrate having a film of 9-fluorenylmethylcarbonyl-diphenylalanine (Fmoc-FF) deposited thereon using a vapor deposition method of an embodiment of the present invention, showing the uniform and homogeneous distribution of the Fmoc-FF film on the glass surface;

FIGS. 7A-B are images of a glass substrate having a film of dityrosine (YY) deposited thereon using vapor deposition method according to some embodiments of the present invention. FIG. 7A is a low magnification optical micrograph showing the uniform and homogeneous distribution of the YY film on the glass surface, and FIG. 7B is a high magnification SEM micrograph showing the fine microstructure of the deposited thin YY film on the glass surface;

FIGS. 8A-B are images of a glass substrate having a film of dialanine (AA) deposited thereon using vapor deposition method according to some embodiments of the present invention. FIG. 8A is a low magnification optical micrograph showing the uniform and homogeneous distribution of the AA film on the glass surface, and FIG. 8B is a high magnification SEM micrograph showing the urchin-like microstructure of the deposited thin AA film on the glass surface;

FIG. 9 is a low magnification optical micrograph of a glass substrate having a uniform and homogeneous film of diglycine (GG) deposited thereon using vapor deposition method according to some embodiments of the present invention;

FIGS. 10A-B are images of a silica substrate having a film of phenylalanine (F) deposited thereon using vapor deposition method according to some embodiments of the present invention. FIG. 10A is a low magnification optical micrograph showing the uniform and homogeneous distribution of F on the silica surface, and FIG. 10B is a high magnification SEM micrograph showing the blob-like microstructure of the deposited thin F film on the glass surface;

FIGS. 11A-C are images of silicon and glass substrates having a film of 3,4-dihydroxy-phenylalanine (DOPA) deposited thereon using a vapor deposition method according to some embodiments of the present invention. FIGS. 11A and 11B are optical micrographs showing the uniform and homogeneous distribution of the DOPA film on silicon and glass respectively, and FIG. 11C is a high magnification SEM micrograph showing the blob-like microstructure of the DOPA film on the glass surface;

FIGS. 12A-C are images of glass and silicon substrates having a film of tryptophan (W) deposited thereon using a vapor deposition method according to some embodiments of the present invention. FIGS. 12A and 12B are optical micrographs of glass and silicon respectively showing the uniform and homogeneous distribution of W deposited thereon, and FIG. 12C is a high magnification SEM micrograph showing the flake-like microstructure of the W film on the glass surface;

FIGS. 13A-C are images of glass and silicon substrates having a film of tyrosine (Y) deposited thereon using a vapor deposition method according to some embodiments of the present invention. FIGS. 13A and 13B are optical micrographs showing the uniform and homogeneous distribution of Y on glass and silicon respectively, and FIG. 13C is a high magnification SEM micrograph showing the needle-like microstructure of the thin Y film deposited on the silicon surface;

FIG. 14 is a low magnification optical micrograph of a glass substrate having a uniform and homogeneous film of triphenylalanine (FFF) deposited thereon using vapor deposition method according to some embodiments of the present invention;

FIG. 15 is a low magnification optical micrograph of a glass substrate having a uniform and homogeneous film of arginine-glycine-aspartic acid (RGD) deposited thereon using vapor deposition method according to some embodiments of the present invention;

FIG. 16 is a low magnification optical micrograph of a glass substrate having a film of polyphenylalanine (Poly-F) deposited thereon using a vapor deposition method according to some embodiments of the present invention, showing a film of Poly-F with interlacing ribs;

FIG. 17 is a low magnification optical micrograph of a glass substrate having a uniform and homogeneous film of bovine serum albumin (BSA) deposited thereon using vapor deposition method according to some embodiments of the present invention;

FIG. 18 is a low magnification optical micrograph of a glass substrate having a uniform and homogeneous film of Fluorescein (FLU) deposited thereon using vapor deposition method according to some embodiments of the present invention;

FIG. 19 is a low magnification optical micrograph of a glass substrate having a uniform and homogeneous film of Calcein (CALC) deposited thereon using vapor deposition method according to some embodiments of the present invention;

FIGS. 20A-C are AFM micrographs of FF-coated glass surfaces, showing the variation in homogeneity and morphology, and the variations in thickness of the deposited biomolecule layer as measured by AFM tapping mode. FIG. 20A shows the FF layer of 50 nm obtained at a vacuum pressure of $10^{-6}$ Torr and a sample heating temperature of 150° C., FIG. 20B shows the FF layer of 1.7 μm obtained at a pressure of $10^{-6}$ Torr and a sample heating temperature of 200° C. and FIG. 20C shows the FF layer of 2.9 μm obtained at a pressure of $10^{-6}$ Torr and a sample heating temperature of 230° C.;

FIGS. 21A-B are SEM micrographs of FF- and DOPA-coated silicon surfaces, showing the variation in morphology of the vapor-deposited biomolecule layer. FIG. 21A shows an FF layer of nanotubes obtained at a vacuum pressure of $10^{-6}$ Torr and a sample heating temperature of 220° C., and FIG. 21B shows a DOPA film of interconnected blobs obtained at a pressure of $10^{-6}$ Torr and a sample heating temperature of 250° C.;

FIGS. 22A-B are SEM micrographs of a biomolecule film (a bio-tape), achieved by removing the vapor deposited F biomolecule layer from a silica substrate with controllable adhesion properties. FIG. 22A shows a front view of the film and FIG. 22B shows a side view thereof;

FIG. 23 is a SEM micrograph of a glass substrate having a micro-pattered FF coat obtained using a shadow mask of silicon with an array of round 100 μm diameter holes;

FIG. 24 is a SEM micrograph of a micro-patterned FF film on a glass substrate obtained using non-filtered Hg—Xe lamp light shone through a hard silicon mask having an array of round 100 μm diameter holes;

FIGS. 25A-B are an optical and SEM images of a $Si_3N_4$ substrate having a film of 9-fluorenylmethylcarbonyl-pentafluorophenylalanine (Fmoc-F5-F) deposited thereon;

FIG. 26 is an optical image of a glass substrate having a film of 9-fluorenylmethylcarbonyl-dipentafluorophenylalanine (Fmoc-F5-FF) deposited thereon;

FIG. 27 is a schematic illustration of an energy storage device, according to various exemplary embodiments of the present invention;

FIG. 28 is a schematic illustration of a sensor device, according to various exemplary embodiments of the present invention;

FIG. 29 is a schematic illustration of another type of sensor device, according to some embodiments of the present invention;

FIGS. 30A-D are images demonstrating the ability of the solid deposition of the present embodiments to form a hydrophobic coat on a substrate;

FIGS. 31A-B demonstrate the ability of the solid deposition of the present embodiments to form a hydrophobic pattern;

FIG. 32 illustrates snapshots of a water droplet before, during, and after initial impact with an Fmoc-F5-FF;

FIG. 33A shows a graphite electrode coated by diphenylalanine, according to various exemplary embodiments of the present invention;

FIG. 33B is a graph showing cyclic voltammetry measurements.

Figure 34A:
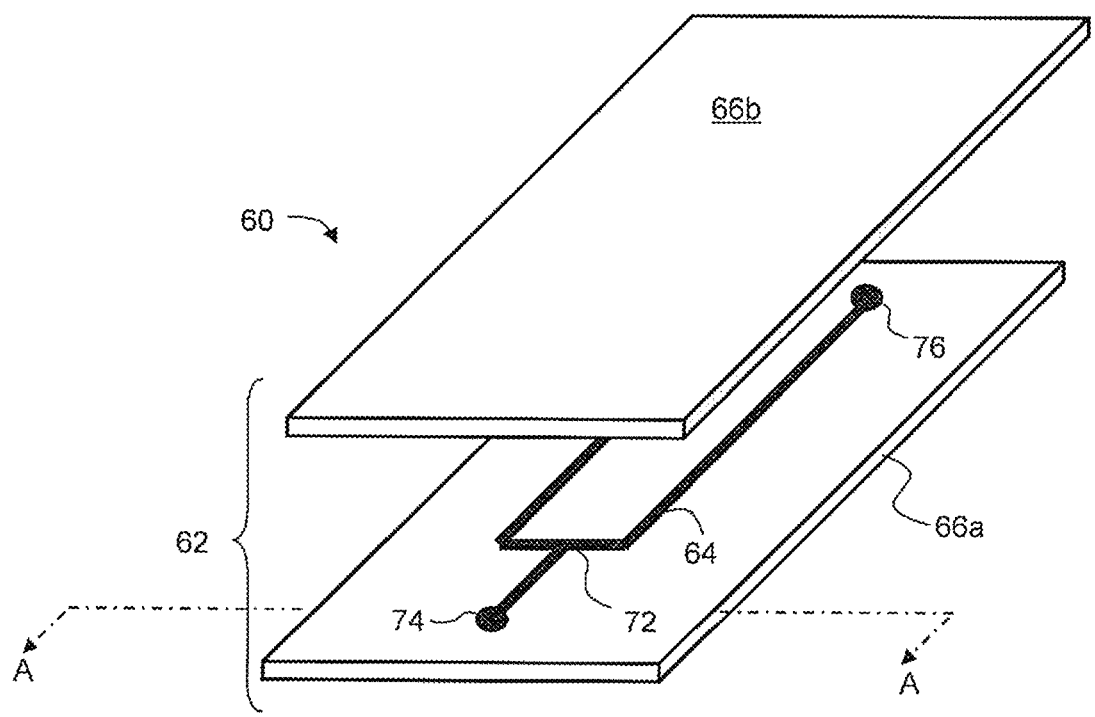
Figure 34B:
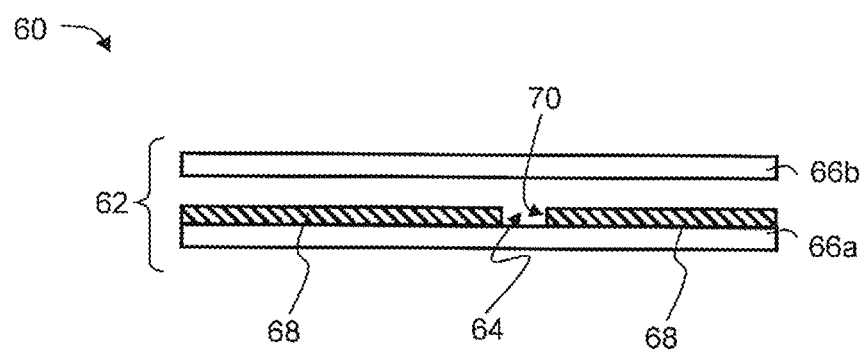
Figure 35:
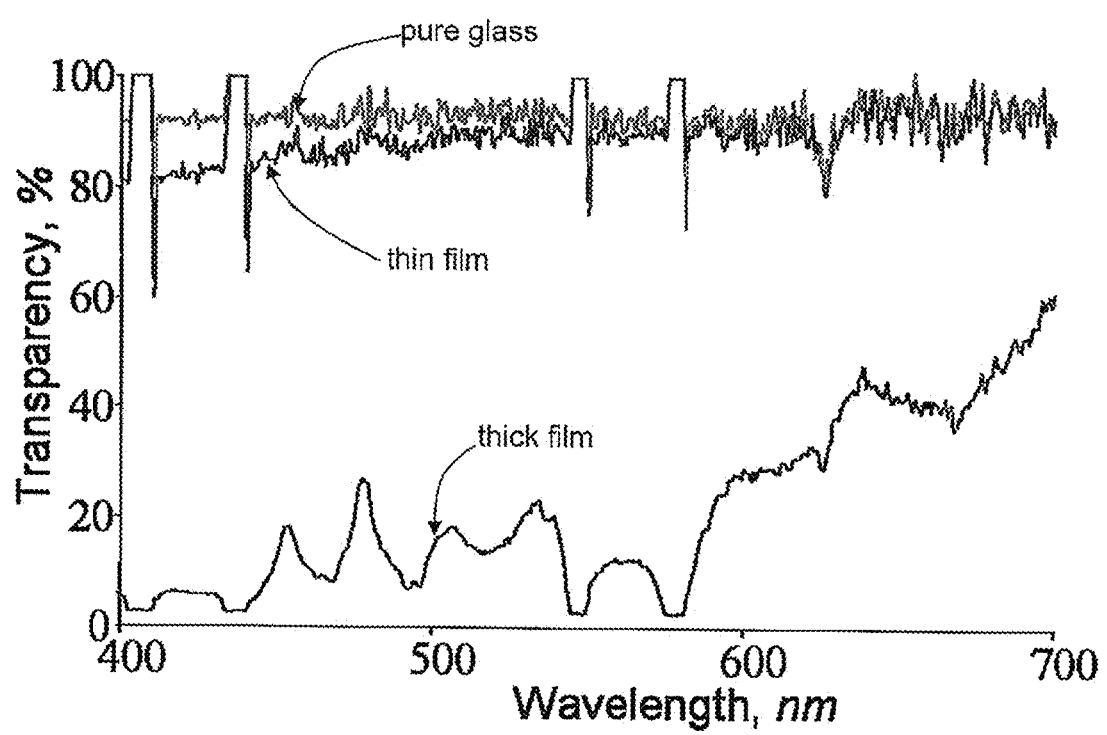

FIGS. 34A-B are schematic illustrations of a microfluidic device 60, according to various exemplary embodiments of the present invention; and FIG. 35 is a graph showing transparency as a function of the wavelength of a glass substrate and glass substrates having thereon solid depositions of FF;

DESCRIPTION OF EMBODIMENTS OF THE INVENTION

The present invention, in some embodiments thereof, relates to applied materials and more particularly, but not exclusively, to vapor deposition techniques utilizing biomolecules such as peptides, and applications thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Biomolecules are organic compounds which have biochemical activity in organisms. Objects coated with a layer of biomolecules and objects made of biomolecules have many uses in research, and many applications such as, but not limited to, medical and industrial applications.

The formation of thin films consisting of biomolecules on the surface of a substrate in accordance with some embodiments of the present invention is a mean to alter the chemical characteristics of the surface such as to render the substrate more compatible with biologic environments and biochemical processes, and provides the surface with enhanced physical characteristics according to the properties of the biomolecules forming the film. Objects coated with thin films of biomolecules and objects made of biomolecules open the way to a multitude of medical, industrial and other biochemical and applied material applications.

The vapor deposition technique employed in accordance with some embodiments of the present invention affords thin film coating of many types of substrates by a variety of coating materials. In general, the coating material passes, at least in some stages of the process, via an uncondensed phase, namely a gaseous phase, wherein it is found at an intermediate state between the coating material sample and the substrate's surface. Typically, high vacuum and elevated temperatures are employed in order to assist the vaporization of the coating material and allow it to deposit on the surface of the substrate.

The terms "biomolecule" and "biological molecule" are used interchangeably herein to refer to any organic molecule that is, was, or can be a part of a living organism, regardless of whether the molecule is naturally occurring, recombinantly produced, or chemically synthesized in whole or in part. Common classes of biomolecules include nucleic acids (and artificial analogs thereof), peptides, lipids, polysaccharides, monosaccharides, amino acids, nucleotides (as well as nucleosides, purines and pyrimidines), flavonoids, isoprenoids, oligomeric species and polymeric species. Preferred classes of biomolecules include peptides, nucleic acids, nucleotides and amino acids as described herein.

One non-limiting example of a family of biomolecules includes amino acids, which are some of the most abundant and prevalent building blocks in nature. Amino acids are monomeric biomolecules that are used to construct polymers known as peptide, dipeptide, oligopeptide, polypeptide and/or protein of all chain length and size.

Another non-limiting example of a family of biomolecules includes nucleotides, which comprise a heteroaryl moiety (a purine or a pyrimidine base), a sugar moiety (pentose sugar) and an inorganic phosphate group. Naturally occurring nucleotides (cytidine, uridine, adenosine, guanosine, thymidine and inosine) are the monomeric biomolecules which are used to construct biomolecular polymers known as nucleic acids (DNA and RNA) of all chain length and sizes. Other exemplary biomolecules include, without limitation, glycoproteins, metalloproteins, lipids, phospholipids, glycolipids, sterols, vitamins, hormones, neurotransmitters, carbohydrates, sugars, monosaccharides (hexoses glucose, fructose, and galactose and pentoses, ribose and deoxyribose), disaccharides (such as sucrose, maltose and lactose), oligosaccharides, polysaccharides (such as starch, cellulose and glycogen), mucopolysaccharides, peptidoglycans, (peptidopolysaccharides) nucleosides and the likes.

The term "biomolecule" as used herein is meant to encompass any functional analog and derivative of a naturally occurring biomolecule.

Many biomolecules are sensitive to harsh chemical and physical conditions such as heat, red-ox conditions, electromagnetic radiation and various expressions thereof. In particular, the conditions during vapor deposition were heretofore considered harmful for biomolecules.

Despite its advanced and widespread use, vapor deposition has not been employed hitherto to coat substrates with biomolecules, particularly since many biomolecules, such as peptides and proteins, are sensitive to the physical conditions employed during the process.

While reducing some embodiments of the present invention to practice, the present inventors have unexpectedly discovered that a sample of biomolecules can be transformed into a vaporized or gaseous state while maintaining the biological properties of the biomolecules in the sample. The present inventors have also found that the ability to transform the biomolecules to a vaporized or gaseous state facilitates their deposition on the surface of a solid substrate. The present inventors have additionally found that biomolecules in a vaporized or gaseous state can be deposited on surfaces to form a solid deposition of nanostructures on the surface.

The present inventors have therefore designed, implemented and successfully practiced vapor deposition of biomolecules on solid surfaces, as presented and exemplified hereinunder.

Hence, according to an aspect of some embodiments of the present invention, there is provided a method for at least partially coating a surface of a substrate with a solid deposition made of one or more types of biomolecules. In some embodiments of the present invention the coating is effected by placing the substrate and one or more samples of the biomolecule in a chamber suitable for a vapor deposition process and applying a vapor deposition process within that chamber so as to deposit the biomolecule(s) on the surface of the substrate. In some embodiments of the present invention the source material is placed in the chamber in solid form (e.g., in the form of a powder).

The solid deposition of the present embodiments typically posses order in the micrometer and sub-micrometer scale. In various exemplary embodiments of the invention the solid deposition is formed of one or more layers of nanostructures which are self-assembled from the biomolecules during or immediately after the deposition process. This can be achieved by judicious selection of the biomolecules and/or substrate, and optionally by executing one or more operations so as to align the self-assembled nanostructures with respect to each other and/or the substrate according to a predetermined alignment.

A solid deposition of nanostructures made of biomolecules is typically characterized by a nanometric pattern which greatly enhances the surface area of the coated substrate. The nanostructures of the solid deposition can be tubular, spherical or they can have any other shape. The advantage of having a solid deposition of such nanostructures is that nanostructures of biomolecules possess superior physical, chemical and thermal stability as well as remarkable mechanical rigidity. Additionally, the nanostructures of the present embodiments have many physical properties such as electronic properties, dielectric properties, electrochemical properties, hydrophobic or hydrophilic properties, etc.

Nanostructures suitable for the present embodiments are disclosed in International Publication Nos. WO 2004/052773, WO 2004/060791, WO 2005/000560 and WO 2006/027780, and International Patent Application No. PCT/IL2007/001495, the contents of which are hereby incorporated by reference.

The nanostructures forming the solid deposition of the present embodiments can be hollow or non hollow. The nanostructures can also be coated by a coating material such as, but not limited to, a conducting material, a semiconducting material, a thermoelectric material, a magnetic material (paramagnetic, ferromagnetic or diamagnetic), a light-emitting material, a biomineral, a dielectric material, a porous material, a polymer and/or an organic material.

In various exemplary embodiments of the invention the nanostructures have a thick wall or a multi-walled structure. This is realized as relatively large ratio between the outer diameter and the diameter of the interior cavity of the nanostructures. In some embodiments of the present invention the ratio between the outer and inner diameters of the nanostructures, is at least 1.5, more preferably at least 2.

In some embodiments of the present embodiments the nanostructure are elongated nanostructures, which are aligned generally parallel to each other, as described in International Patent Application No. PCT/IL2007/001495 supra. The nanostructures can engage a single plane, thus forming a “monolayer” of nanostructures), or they can engage a plurality planes or a bulk, thus forming a “forest” of nanostructures). For example, in some embodiments of the present invention the nanostructures are arranged on a substrate generally perpendicularly to the substrate. In other embodiments, the nanostructures are arranged generally parallel to the substrate.

In some embodiments of the present embodiments the biomolecules are electrically charged. This is particularly useful in application in which it is desired to have a solid deposition of nanostructures having a generally uniform orientation. The existence of electric charges establishes repulsion or attraction electrical forces which facilitate such orientation. For example, in some embodiments of the present invention, the biomolecules and/or substrate are preferably selected to establish repulsion forces between the biomolecules and the substrate hence to facilitate a generally vertical build-up of nanostructures on the substrate.

In some embodiments of the present invention, the biomolecules or self-assembled nanostructures are responsive to a force field, such as an electrostatic or magnetic field. For example, when the biomolecules or self-assembled nanostructures are electrically charged, they are responsive to an electrostatic field; when the biomolecules or self-assembled nanostructures are, e.g., diamagnetic, they are responsive to a magnetic field.

In some embodiments of the present invention, the vapor deposition process is can also involve an additional material which is responsive to the force field. In these embodiments, the vapor deposition process can be a chemical vapor deposition process in which case a chemical reaction takes place between the additional material and the biomolecules within the chamber.

During or subsequently to the vapor deposition process, the force field is applied such as to align the nanostructures generally parallel to each other. Optionally, the force field is directed generally parallel to the surface of the substrate, such that the solid deposition includes nanostructures which are aligned parallel to the surface. Alternatively, the force field is directed generally perpendicular to the surface of the substrate, such that the solid deposition includes nanostructures which are generally vertical with respect to the surface.

The solid deposition of the present embodiments can take any shape or form, such as, for example, a line, a stripe, a streak, a dot, a patch, a tube, a layer, a coat or a film, as well as combinations and multiples thereof. For example, a coat may comprise more than one layer, and in some embodiments, at least two adjacent layers are formed of different type of biomolecule. In some embodiments, more than one vapor deposition process can be employed for the same coat. For example, one vapor deposition process can be employed to form one layer and another, different, vapor deposition process can be employed to form the subsequent layer. Also contemplated is a multilayer coat in which one or more of the layers are formed via process other than vapor deposition. For example, one layer can be formed via electroplating, and a subsequent layer can be formed via vapor deposition. In some embodiment of the present invention, the vapor deposition process is followed by an additional coating process (e.g., electroplating), where the solid deposition is coated, at least partially, by another material. For example, once solid deposition of nanostructures is formed by vapor deposition, it can be coated or partially coated by a coating material such as, but not limited to, a conducting material, a semiconducting material, a thermoelectric material, a magnetic material (paramagnetic, ferromagnetic or diamagnetic), a light-emitting material, a biomineral, a dielectric material, a porous material, a polymer and/or an organic material.

Vapor deposition (VD) refers to a process in which materials in a vapor state are condensed through condensation, chemical reaction or conversion to form a solid material. VD is used to form coatings to alter the mechanical, electrical, thermal, optical, corrosion resistance, and wear properties of the coated substrates, as well as to form free-standing bodies, films, and fibers and to infiltrate fabric to form composite materials. VD processes typically take place within a vacuum chamber, and are classified into two process categories: physical vapor deposition (PVD) and chemical vapor deposition (CVD).

In PVD, there is typically a single source material which is vaporized and deposited over the substrate. The source PVD methods are clean, dry vacuum deposition methods in which the coating is deposited over the entire object simultaneously, rather than in localized areas. PVD covers a number of deposition technologies in which material is released from a source and transferred to the substrate. The vapor can be generated thermally thus these techniques are called evaporation of layer material. Yet, condensable particles can also be generated by pulse transmission during bombardment with high-energy ions. Such process is also known as sputtering. The choice of deposition method, namely evaporation or sputtering, depends mostly on the coating and coated materials and the availability of a technology for these specific materials.

In evaporation-based techniques the substrate is placed inside a vacuum chamber, in which a source material to be deposited is also located. The source material is then heated to the point where it starts to evaporate. Vacuum is required to allow the molecules to evaporate freely in the chamber, and they subsequently condense on all surfaces. The evaporation technique may include electron beam evaporation and resistive evaporation. In electron beam evaporation, an electron beam is aimed at the source material causing local heating and evaporation. In resistive evaporation, electrical current heats a resistor such as tungsten which is in thermal contact with the source material. The amount of heat is selected to evaporate the material.

In sputtering-based techniques the material is released from the source at much lower temperature than evaporation. The substrate is placed in a vacuum chamber with the source material, and an inert gas (such as argon) is introduced at low pressure. Gas plasma is struck using a radiofrequency power source, causing the gas to become ionized. The ions are accelerated towards the surface of the source material, causing atoms of the source material to break off in vapor form and condense on all surfaces including the substrate. As in evaporation-based techniques, the basic principle of sputtering is the same for all sputtering technologies, while various approaches differ in the way the ion bombardment of the source material is effected.

Table 1 below presents a brief description of the possibilities to generate vapors.

TABLE 1

| | Evaporation |
|---|---|
| Indirect method | Heating by heating spiral, heated boats and crucible |
| Direct method | Heating of the material to be evaporated by current passage induction, arc discharge, electron impact, laser radiation |
| Combination of direct and indirect method | Current passage through crucible and material to be evaporated |
| | Sputtering |
| Cathodic sputtering | DC gas discharge, the material to be sputtered is connected as cathode; for insulators HF gas discharge |
| Ion beam sputtering | Ion bombardment from an ion source |

In PVD, there are typically two or more source materials which is are vaporized and a chemical reaction takes place between the vaporized source materials prior to, during and/or subsequently to their deposition over the substrate. The product of that reaction is a solid material with condenses on all surfaces inside the reactor. Depending on the process and operating conditions, the reactant gases may undergo homogeneous chemical reactions in the vapor phase before striking the surface. Various CVD techniques are contemplated, including, without limitation, atmospheric pressure chemical vapor deposition (APCVD), low pressure chemical vapor deposition (LPCVD), plasma assisted (enhanced) chemical vapor deposition (PACVD, PECVD), photochemical vapor deposition (PCVD), laser chemical vapor deposition (LCVD), metal-organic chemical vapor deposition (MOCVD), chemical beam epitaxy (CBE), and chemical vapor infiltration (CVI).

The method according to some embodiments of the present invention results in a composition-of-matter which is essentially composed of the substrate having a coat of biomolecules, as defined hereinabove, deposited thereon. Hence, according to another aspect of the present invention, there is provided a composition-of-matter which includes a biomolecule, or more than one type thereof, and a solid substrate having thereon a solid deposition of the biomolecule(s) deposited by vapor deposition and occupying at least a portion of a surface of the substrate.

According to some embodiments, the biomolecule is a peptide. In these embodiments the composition-of-matter includes a substrate having thereon a solid deposition of a peptide, deposited by vapor deposition and occupying at least a portion of a surface of the substrate.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body. Such modifications include, but are not limited to N terminus modification, C terminus modification, peptide bond modification, including, but not limited to, $CH_2-NH$, $CH_2-S$, $CH_2-S=O$, $O=C-NH$, $CH_2-O$, $CH_2-CH_2$, $S=C-NH$, $CH=CH$ or $CF=CH$, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N—methylated bonds (—N(CH$_3$)—CO—), ester bonds (—C(R)H—C—O—O—C(R)—N—), ketomethylen bonds (—CO—CH$_2$—), α-aza bonds (—NH—N(R)—CO—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—CO—), peptide derivatives (—N(R)—CH$_2$—CO—), wherein R is the "normal" side chain, naturally presented on the carbon atom.

These modifications can occur at any of the bonds along the peptide chain and even at several (2-3) at the same time.

The peptides forming the nanostructures of the present embodiments typically comprise from 2 to 15 amino acid residues. More preferably, the peptides are short peptides of less than 10 amino acid residues, more preferably less than 8 amino acid residues and more preferably are peptides of 2-6 amino acid residues, and hence each peptide preferably has 2, 3, 4, 5, or 6 amino acid residues.

As used herein the phrase "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Natural aromatic amino acids, Trp, Tyr and Phe, may be substituted for synthetic non-natural acid such as Phenylglycine, TIC, napthylalanine (Nal), phenylisoserine, threoninol, ring-methylated derivatives of Phe, halogenated derivatives of Phe or O-methyl-Tyr and -amino acids.

The peptides of the present embodiments may include one or more modified amino acids or one or more non-amino acid monomers (e.g. fatty acids, complex carbohydrates etc).

The peptides utilized for forming the nanostructures of the present embodiments are typically linear peptides. Yet, cyclic forms of the peptide are not excluded from the scope of the present invention.

In some embodiments of the present invention the peptides composing the peptide nanostructures of the present embodiments comprise one or more aromatic amino acid residue. The advantage of having such peptides is that the aromatic functionalities which are built into the peptide allow the various peptide building blocks to interact through attractive aromatic interactions, to thereby form the nanostructure.

The phrase "aromatic amino acid residue", as used herein, describes an amino acid residue that has an aromatic moiety, as defined herein, in its side-chain.

Thus, according to some embodiments of the present invention, each of the peptides composing the peptide nanostructures comprises the amino acid sequence X-Y or Y-X, wherein X is an aromatic amino acid residue and Y is any other amino acid residue.

The molecules of the present invention can be a single amino acid or a peptide composed of least 2 amino acids in length.

In some embodiments of the present invention, one or several of the peptides forming the nanostructures is a polyaromatic peptide, which comprises one, two or more aromatic amino acid residues.

As used herein the phrase "polyaromatic peptides" refers to peptides which include at least 80%, more preferably at least 85%, more preferably at least 90%, more preferably at least 95% or more aromatic amino acid residues. In some embodiments, at least one peptide consists essentially of aromatic amino acid residues. In some embodiments, each peptide consists essentially of aromatic amino acid residues.

Thus for example, the peptides used for forming the nanostructures can include any combination of: dipeptides composed of one or two aromatic amino acid residues; tripeptides including one, two or three aromatic amino acid residues; and tetrapeptides including two, three or four aromatic amino acid residues and so on.

In some embodiments of the present invention, the aromatic amino acid can be any naturally occurring or synthetic aromatic residue including, but not limited to, phenylalanine, tyrosine, tryptophan, phenylglycine, or modificants, precursors or functional aromatic portions thereof.

In some embodiments, one or more peptides in the plurality of peptides used for forming the nanostructures include two amino acid residues, and hence is a dipeptide.

In some embodiments, each of the peptides used for forming the nanostructures comprises two amino acid residues and therefore the nanostructures are formed from a plurality of dipeptides.

Each of these dipeptides can include one or two aromatic amino acid residues. Preferably, but not obligatorily each of these dipeptides includes two aromatic amino acid residues. The aromatic residues composing the dipeptide can be the same, such that the dipeptide is a homodipeptide, or different. In some embodiments, the nanostructures are formed from homodipeptides.

Hence, in various exemplary embodiments of the invention each peptide in the plurality of peptides used for forming the nanostructures is a homodipeptide composed of two aromatic amino acid residues that are identical with respect to their side-chains residue.

The aromatic amino acid residues used for forming the nanostructures can comprise an aromatic moiety, where the phrase "aromatic moiety" describes a monocyclic or polycyclic moiety having a completely conjugated pi-electron system. The aromatic moiety can be an all-carbon moiety or can include one or more heteroatoms such as, for example, nitrogen, sulfur or oxygen. The aromatic moiety can be substituted or unsubstituted, whereby when substituted, the substituent can be, for example, one or more of alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

Exemplary aromatic moieties include, for example, phenyl, biphenyl, naphthalenyl, phenanthrenyl, anthracenyl, [1,10]phenanthrolinyl, indoles, thiophenes, thiazoles and, [2,2']bipyridinyl, each being optionally substituted. Thus, representative examples of aromatic moieties that can serve as the side chain within the aromatic amino acid residues described herein include, without limitation, substituted or unsubstituted naphthalenyl, substituted or unsubstituted phenanthrenyl, substituted or unsubstituted anthracenyl, substituted or unsubstituted [1,10]phenanthrolinyl, substituted or unsubstituted [2,2']bipyridinyl, substituted or unsubstituted biphenyl and substituted or unsubstituted phenyl.

The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine. When substituted, the phenyl, naphthalenyl or any other aromatic moiety includes one or more substituents such as, but not limited to, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

Representative examples of homodipeptides that can be used to form the nanostructures of the present embodiments include, without limitation, a naphthylalanine-naphthylalanine dipeptide, phenanthrenylalanine-phenanthrenylalanine dipeptide, anthracenylalanine-anthracenylalanine dipeptide, [1,10]phenanthrolinylalanine-[1,10]phenanthrolinylalanine dipeptide, [2,2']bipyridinylalanine-[2,2']bipyridinylalanine dipeptide, (pentahalo-phenylalanine)-(pentahalo-phenylalanine)dipeptide, phenylalanine-phenylalanine dipeptide, (amino-phenylalanine)-(amino-phenylalanine)dipeptide, (dialkylamino-phenylalanine)-(dialkylamino-phenylalanine)dipeptide, (halophenylalanine)-(halophenylalanine) dipeptide, (alkoxy-phenylalanine)-(alkoxy-phenylalanine) dipeptide, (trihalomethyl-phenylalanine)-(trihalomethyl-phenylalanine)dipeptide, (4-phenyl-phenylalanine)-(4-phenyl-phenylalanine)dipeptide and (nitro-phenylalanine)-(nitro-phenylalanine)dipeptide.

In some embodiments of the present invention one or more biomolecules, particularly, but not obligatorily peptides, is modified by end-capping.

The phrase "end-capping modified peptide", as used herein, refers to a peptide which has been modified at the N-(amine)terminus and/or at the C-(carboxyl)terminus thereof. The end-capping modification refers to the attachment of a chemical moiety to the terminus, so as to form a cap. Such a chemical moiety is referred to herein as an end-capping moiety and is typically also referred to herein and in the art, interchangeably, as a peptide protecting moiety or group.

The phrase "end-capping moiety", as used herein, refers to a moiety that when attached to the terminus of the peptide, modifies the end-capping. The end-capping modification typically results in masking the charge of the peptide terminus, and/or altering chemical features thereof, such as, hydrophobicity, hydrophilicity, reactivity, solubility and the like. Examples of moieties suitable for peptide end-capping modification can be found, for example, in Green et al., "Protective Groups in Organic Chemistry", (Wiley, second ed. 1991) and Harrison et al., "Compendium of Synthetic Organic Methods", Vols. 1-8 (John Wiley and Sons, 1971-1996).

The use of end-capping modification, allows to control the chemical properties and charge of the nanostructures, hence also the way the peptide nanostructures of the present embodiments are assembled and/or aligned.

Changing the charge of one or both termini of one or more of the peptides may result in altering the morphology of the resulting nanostructure and/or the way the resulting nanostructure responds to, for example, an electric and/or magnetic fields.

End-capping of a peptide can be used to modify its hydrophobic/hydrophilic nature. Altering the hydrophobic/hydrophilic property of a peptide may result, for example, in altering the morphology of the resulting nanostructure and/or the aqueous solubility thereof. By selecting the percentage of the end-capping modified peptides and the nature of the end capping modification, the hydrophobicity/hydrophilicity, as well as the solubility of the nanostructure can be finely controlled. For example, the end capping modification can be selected to control adherence of nanoparticles to the wall of the nanostructures.

While reducing the present invention to practice, the present inventors have uncovered that modifying the end-capping of a peptide does not abolish its capacity to self-assemble into nanostructures, similar to the nanostructures formed by unmodified peptides. The persistence of the end-capping modified peptides to form nanostructures supports the hypothesis of the present inventors according to which the dominating characteristic required to form peptides nanostructures is the aromaticity of its side-chains, and the π-stacking interactions induced thereby, as previously described in, for example WO 2004/052773 and WO 2004/060791, the contents of which are hereby incorporated by reference.

It was further found by the present inventors that the aromatic nature of at least one of the end-capping of the peptide affects the morphology of the resulting nanostructure. For example, it was found that an unmodified peptide or a peptide modified with a non-aromatic end-capping moiety can self-assemble to a tubular nanostructure.

Representative examples of N-terminus end-capping moieties suitable for the present embodiments include, but are not limited to, formyl, acetyl (also denoted herein as "Ac"), trifluoroacetyl, benzyl, benzyloxycarbonyl (also denoted herein as "Cbz"), tert-butoxycarbonyl (also denoted herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

Representative examples of C-terminus end-capping moieties suitable for the present embodiments are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

Other end-capping modifications of peptides include replacement of the amine and/or carboxyl with a different moiety, such as hydroxyl, thiol, halide, alkyl, aryl, alkoxy, aryloxy and the like, as these terms are defined herein.

In some embodiments of the present invention, all of the peptides that form the nanostructures are end-capping modified.

End-capping moieties can be further classified by their aromaticity. Thus, end-capping moieties can be aromatic or non-aromatic.

Representative examples of non-aromatic end capping moieties suitable for N-terminus modification include, without limitation, formyl, acetyl trifluoroacetyl, tert-butoxycarbonyl, trimethylsilyl, and 2-trimethylsilyl-ethanesulfonyl. Representative examples of non-aromatic end capping moieties suitable for C-terminus modification include, without limitation, amides, allyloxycarbonyl, trialkylsilyl ethers and allyl ethers.

Representative examples of aromatic end capping moieties suitable for N-terminus modification include, without limitation, fluorenylmethyloxycarbonyl (Fmoc). Representative examples of aromatic end capping moieties suitable for C-terminus modification include, without limitation, benzyl, benzyloxycarbonyl (Cbz), trityl and substituted trityl groups.

When the nanostructures of the present embodiments comprise one or more dipeptides, the dipeptides can be collectively represented by the following general Formula I:

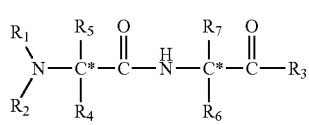

Formula I where:

$C^*$ is a chiral carbon having a D configuration or L configuration; $R_1$ and $R_2$ are each independently selected from the group consisting of hydrogen, alkyl, cycloalkyl, aryl, carboxy, thiocarboxy, C-carboxylate and C-thiocarboxylate; $R_3$ is selected from the group consisting of hydroxy, alkoxy, aryloxy, thiohydroxy, thioalkoxy, thioaryloxy, halo and amine; and each of $R_4$-$R_7$ is independently selected from the group consisting of hydrogen, alkyl, cycloalkyl, aryl, heteroaryl, heteroalicyclic, hydroxy, thiohydroxy (thiol), alkoxy, aryloxy, thioalkoxy, thioaryloxy, C-carboxylate, C-thiocarboxylate, N-carbamate, N-thiocarbamate, hydrazine, guanyl, and guanidine, as these terms are defined herein, provided that at least one of $R_4$-$R_7$ comprises an aromatic moiety, as defined hereinabove.

Also contemplated are embodiments in which one or more of $R_4$-$R_7$ is other substituent, provided that at least one comprises an aromatic moiety.

Also contemplated are embodiments in which one or more of $R_1$-$R_3$ is the end-capping moieties described hereinabove.

The peptide nanostructures of the present embodiments can further comprise a functional group, preferably a plurality of functional groups.

The functional group can be, for example, a group such as, but not limited to, thiol, hydroxy, halo, carboxylate, amine, amide, nitro, cyano, hydrazine, and the like, a hydrophobic moiety, such as, but not limited to, medium to high alkyls, cycloalkyls and aryls, and/or a metal ligand.

The substrate, according to some embodiments of the present invention, can be any solid object having any size, shape of form, and having at least a portion of its surface accessible and free for allowing a biomolecule to be deposited thereon. The material of the substrate can be metal, metalloid and/or alloys such as, without limitation, titanium, copper, silver, gold, nickel, silicon and the likes; mineral such as, without limitation, glass, silica, quartz, $Si_3N_4$, calcium phosphates, hydroxyapatite ceramics (HAp), ferroelectric crystals (such as $LiNbO_3$) and the likes; carbon-based solids such as, without limitation, graphite, polymers and other carbon-based solid composites. In some embodiments of the present invention the substrate is transmissive to visible light.

According to some embodiments of the present invention, the vapor deposition process is carried out in a vapor deposition system under vacuum conditions so as to lower the vaporization temperature of the biomolecule. Hence, the chamber used for the vapor deposition process is preferably a sealed vacuum chamber, suitable for applying vacuum therein.

Most typical biomolecules have a relatively low vapor pressure, and therefore the vacuum which is applied to the chamber is typically high vacuum, in the range of about $10^{-4}$ Torr to about $10^{-8}$ Torr. High vacuum is typically achieved by means of a turbo-molecular pump, or TMP, which is part of the vapor deposition system according to some embodiments of the present invention.

Following the lowering of pressure in the chamber, the sample(s) of the biomolecule is heated so as to increase the vapor pressure thereof. The vapor deposition system of some embodiments of the present invention is equipped with a heating unit for heating the biomolecule sample(s) to a temperature that ranges from ambient temperature to about 1000° K. (about 1273° C.). The rate of the temperature variation and temperature of biomolecules deposition can be judiciously selected for deposition of coating with controllable thickness and homogeneity.

According to some embodiments of the present invention, the system includes a substrate holder for holding the substrate onto which the deposition of the biomolecule(s) is effected. In order to control the deposition process and the resulting solid deposition of the biomolecule(s), the substrate holder can be heated or cooled e.g., using a controllable cooling/heating element.

Referring now to the drawings, FIG. 1 is an image of an exemplary experimental setup for biomolecules vapor deposition system, according to some embodiments of the present invention. In the representative example shown in FIG. 1, the setup includes a vacuum chamber 1, a vacuum gauge 2, a heating/cooling unit 3, a substrate holder 4, a thermocouple 5, a vacuum pump system 6, a sample holder 7, a cartridge heater 8 and a control unit 9. The setup can also include other components.

In experiments performed by the present Inventors, the deposition procedure of biomolecules was employed in vacuum chamber 1, which contained several individual ports for vacuum gauge 2. Vacuum pressure of up to $10^{-8}$ Torr was provided by a vacuum turbo-molecular pump system (vacuum pump 6) by Pfeiffer, Germany. Heating/cooling unit 3 allowed performing biomolecules vapor deposition in wide range of temperatures, raging from about 100° K. to about 1000° K., and consisted of sample holder 7 which contained the biomolecule sample that underwent evaporation due to heating of sample holder 7, and a copper tube onto which a mobile cartridge heater 8 was mounted. The temperature was varied at a rate ranging from 1° K./min to 30° K./min. Controlling and monitoring the temperature, the rate of temperature variation and the vacuum pressure was effected by control unit 9.

It should be noted that any setup, system and process allowing vapor deposition of biomolecules can be used, and therefore such processes are encompassed by the present invention. For each setup, system and process, the parameters of biomolecules vapor deposition, such as heating/cooling temperature, heating rate, quantity and concentration of the biomolecule sample, distance between the substrate and the biomolecule sample, temperature of the sample holder, vacuum depth and the like, can be adapted to suit biomolecules of different origin and structures in order to fabricate coatings of different sorts such as thin films of predetermined thicknesses, self-assembly or/and patterned structures with micro- to nano-scale features.

Once the vapor deposition process is completed and the coated substrate is removed from the system, the solid deposition which was formed thereon during the deposition process can be detached therefrom while retaining at least some of the original form and shape of the solid deposition, thereby affording a stand-alone object, or article-of-manufacture, which is made of the biomolecule(s) and lacking the substrate.

Hence, according to another aspect of the present invention, there is provided an article-of-manufacture which includes a solid deposition of a biomolecule, or more than one type thereof, being formed by vapor deposition as presented herein and devoid of any solid substrate attached thereto. According to some embodiments, the biomolecule is a peptide.

Accordingly, there is provided a process of manufacturing an article-of-manufacture presented hereinabove. The process can begin in a vapor deposition step in which a solid deposition of biomolecules is deposited onto at least a portion of a surface of a solid substrate to thereby form a solid deposition of the biomolecule(s). The process continues to a detachment step in which the solid deposition is detached from the surface, thereby to obtain an article-of-manufacture devoid of solid substrate attached thereto.

As presented and demonstrated in the Examples section that follows below (see, e.g., FIG. 22), using the above-mentioned process, a free standing film can be achieved by physical separation/removing the vapor-deposited phenylalanine layer from a silica substrate having low adhesion properties.

According to some embodiments of the present invention the thickness of solid deposition of biomolecules is controlled by judicious selection of one or more of the parameters characterizing the vapor deposition process. According to some embodiments of the present invention, the solid deposition is characterized by a thickness ranging from about 10 nm to about 10 µm or more. In various exemplary embodiments of the invention the thickness is at least 1 m or at least 5 m or at least 10 m.

As discussed herein and demonstrated in the Examples section that follows, the solid deposition of biomolecules can be characterized by micro-structural features, such as a smooth coat, a dotted (e.g., splashy, spotty, specked, speckled, spotted, ocellar) coat (see FIGS. 7B and 11B), a fibrous (e.g., filamentary, filamentous, fibroid, scirrhous, stringy, thready) coat (see FIG. 10B), a thin film, a flaky (e.g., peel-like, scale-like, chip-like, stratum-like) coat (see FIGS. 5B, 12C and 21A), a layered coat, a lines-furrowed or streaks-furrowed coat (see FIGS. 15 and 16), a rods-covered or a needles-covered surface (see FIGS. 2B, 7B and 13C), a spheroids-covered surface, a patchy coat, a streaky or a striped coat, a tape (see FIG. 22), a tube, or various combinations thereof.

As discussed herein and demonstrated in the Examples section that follows, the solid deposition of biomolecules is further characterized by macro-structural features, such as a pattern of biomolecules coating the substrate. The pattern can be a spontaneous pattern as well as a predetermined pattern, which follows a predetermined design of a mold and/or a model.

The predetermined pattern, according to some embodiments of the present invention, can comprise a single layer of a vapor deposited biomolecule, forming a predetermined two-dimensional interspersion on the surface of the substrate.

Alternatively, the predetermined pattern can comprise multiple layers, optionally of more than one type of biomolecules, which form a three-dimensional spatial interspersion of the solid deposition on the surface (or part thereof).

In both the two-dimensional and three-dimensional patterns which can be deposited onto the surface of a substrate, the pattern can be characterized, among other criteria, as an array of discrete and distinct addressable locations. Such a pattern is particularly useful in the manufacturing of miniaturized electrical circuitry and templates thereof, area and spatial detectors, sensors, biosensors and templates thereof, fabrication of nano-patterned bio-structures and templates thereof, fabrication of nano-patterned bio-structures and templates for gases adhesion (air purification), fabrication of bio-structures and templates for contaminants selective adhesion (water and other liquids purification), fabrication of transmissive coats, such as hydrophobic or superhydrophobic coats for self-cleaning surfaces (e.g., the so called "smart window") and solar cells, fabrication of coats with controllable properties (transparency, reflectivity and/or absorption) for various electromagnetic radiation ranges (X-ray, UV, visible, IR, RF), fabrication of electrochemical devices including batteries, accumulators, capacitors and other electrical storage devices, fabrication of microfluidic devices, engineering of biological surfaces including tissue engineering and patterned biological cues, fabrication of bio-structures and templates for cell growth confinement, fabrication of bio-structures and templates for specific biomolecules coatings for gas storage, ion exchange, various catalysis, guest adsorption, and the likes.

In some embodiments of the present invention the gap between any two adjacent locations out of the plurality of locations is at least 10 nm.

Accordingly, there is provided a method of coating at least a portion of a surface of a substrate with a solid deposition of at least one type of a biomolecule, which is effected by subjecting the substrate and the biomolecule(s) to a vapor deposition process so as to deposit the biomolecule(s) on the substrate according to a predetermined pattern.

The process of vapor deposition of the patterned solid deposition of biomolecules can be similar to the process of coating the same surface without the pattern, with the exception that the deposition process further involves forming a pattern, during or after the solid deposition. For example, the surface can be masked by a mask prior to depositing the biomolecule(s), so as to allow selective coating.

The shadow mask can be in the form of a plate with one or more openings and foramens having a particular shape, arranged in a particular pattern. Alternatively the mask can be a plate having transparent and opaque areas arranged in a particular pattern. Also contemplated, is a hard mask which is applied to the substrate by lithography methods prior to the vapor deposition process and removed from the substrate thereafter.

Thus, a patterned solid deposition of biomolecules can be formed by placing a mask over the substrate before the biomolecule is deposited thereon, such as to allow deposition along the desired pattern and substantially prevent deposition on other areas.

Such a patterned deposition is demonstrated in the Examples section that follows, as shown in FIG. 23. This patterned deposition was afforded by placing a shadow silicon mask having an array of round holes over a glass substrate prior to depositing diphenylalanine thereon, thereby allowing the deposition to occur only at locations corresponding to the holes in the mask.

According to some embodiments of the present invention, the process further includes, subsequent to the deposition of the biomolecule(s), masking the surface having a solid deposition already deposited thereon by a mask and applying radiation to the mask so as to form a patterned solid deposition. In these embodiments the pattern is formed by diminution of the solid deposition by degradation thereof as a result of irradiation.

As used herein, the term "radiation" refers to energy which can be directly irradiated onto an area in the form of electromagnetic waves or particles. The act of applying non-ionizing or ionizing radiation (irradiation) onto the solid deposition of biomolecule(s) degrades the solid deposition; hence the radiation is selected such that it can effect such local and controllable degradation.

Such a patterned deposition is demonstrated in the Examples section that follows, as can be seen in FIG. 24. This patterned deposition was afforded by placing a hard silicon mask having an array of round 100 μm diameter holes over a glass substrate which was previously coated via vapor deposition with a solid deposition of diphenylalanine. The mask was irradiated with non-filtered Hg—Xe lamp light to pattern the deposition with holes in accordance with the locations of the holes in the mask.

The biomolecule(s) can be selected so as to have a particular biologic activity, such as a therapeutic activity, antimicrobial activity, agonistic or antagonistic activity or an inhibitory or stimulatory activity with respect to a particular biologic target, and various other desired effects. A medical device, and particularly an implantable medical device which is partly or entirely coated with a biomolecule by vapor deposition may have an improved function or a unique functionality by virtue of this coat.

Hence, according to another aspect of the present invention, there is provided a medical device which includes a biomolecule and a solid substrate having thereon a solid deposition of the biomolecule deposited by vapor deposition and occupying at least a portion of a surface of the substrate.

The medical device of some embodiments of the present invention can be used for delivering to or applying on a desired bodily site the biomolecule(s). Thus, the medical device can serve as AN intracorporeal vehicle.

As used herein, the phrase "bodily site" includes any organ, tissue, membrane, cavity, blood vessel, tract, biological surface or muscle, which delivering thereto or applying thereon the polymers of the present invention is beneficial.

Exemplary bodily sites include, but are not limited to, the skin, a dermal layer, the scalp, an eye, an ear, a mouth, a throat, a stomach, a small intestines tissue, a large intestines tissue, a kidney, a pancreas, a liver, the digestive system, the respiratory tract, a bone marrow tissue, a mucosal membrane, a nasal membrane, the blood system, a blood vessel, a muscle, a pulmonary cavity, an artery, a vein, a capillary, a heart, a heart cavity, a male or female reproductive organ and any visceral organ or cavity.

According to some embodiments of the present invention, the medical device is designed for implanting the medical device in a bodily organ. As used herein, the term "organ" further encompasses a bodily cavity.

The organ can be, for example, a pulmonary cavity, a heart or heart cavity, a bodily cavity, an organ cavity, a blood vessel, an artery, a vein, a muscle, a bone, a kidney, a capillary, the space between dermal layers, an organ of the female or male reproductive system, an organ of the digestive tract and any other visceral organ.

The medical device according to this embodiment of the present invention typically includes a device structure onto which a biomolecule is deposited on at least parts of its surface. The device structure can be, for example, metallic structure and thus may be comprised of a biocompatible metal or mixture of metals such as gold or platinum. Alternatively, the device structure may be comprised of other biocompatible matrices. These can include, for example, plastics, glass, silicon, polymers, resins, and may include at least one component such as, for example, polyurethane, cellulose ester, polyethylene glycol, polyvinyl acetate, dextran, gelatin, collagen, elastin, laminin, fibronectin, vitronectin, heparin, segmented polyurethane-urea/heparin, poly-L-lactic acid, fibrin, cellulose and amorphous or structured carbon such as in fullerenes, and any combination thereof.

In cases where a biodegradable implantable device is desired, the device structure can be comprised of a biocompatible matrix that is biodegradable. Biodegradable matrices can include, for example, biodegradable polymers such as poly-L-lactic acid.

Optionally, the device structure may be comprised of biocompatible metal(s) coated with other biocompatible matrix.

Further optionally, in cases where a device which can release the biomolecule(s) in a controlled manner is desired, the device structure can be comprised of or be coated with a biocompatible matrix that functions as or comprises a slow release carrier. The biocompatible matrix can therefore be a slow release carrier which is dissolved, melted or liquefied upon implantation in the desired site or organ. Further alternatively, the biocompatible matrix can comprise a biodegradable matrix, which upon degradation releases the deposited biomolecule(s).

The substrate coated with a biomolecule by vapor deposition can be used to form a part of an electrical energy storage device, such as, but not limited to, electrical cell, electrochemical cell or power source. Since the solid deposition surface of the present embodiments is made of nanostructures of biomolecules, it has high relative surface area. The solid deposition surface of the present embodiments can also possess high activity and density rate, high heat dissipation rate and/or high dispersion rate. Additionally, the nanostructures in the solid deposition of the present embodiments facilitate quantum sizing effect, micro sizing effect, surface effect and/or macroscopic quantum tunneling. Such properties make the solid deposition surface useful in production of cells having high charging current that allows fast charging of the energy storage devices.

Two types of electrical energy storage devices are contemplated by the present embodiments. In some embodiments, the electrical energy storage device is embodied as a battery device whereby charge storage is achieved via electron transfer that produces a redox reaction. In some embodiments, the electrical energy storage device is embodied as an electric double-layer capacitor, also known as a supercapacitor, whereby the storage of electrical energy is electrostatic, substantially devoid of any electron transfer.

To avoid possible confusion between a single cell and electrical energy storage device which may have one or more cells, the terms "cell" and electrical energy storage device are used interchangeably, except where the context clearly indicates otherwise. As used herein the term "electrode" is used to mean a phase through which charge is carried by electronic movement. Electrodes can be metals or semiconductors, and they can be solid or liquid. Also as used herein, the term "electrolyte" is generally defined as a phase through which charge is carried by the movement of ions. Electrolytes may be any phase on the continuum of liquid to solid, including gels, pastes, fused salts, or ionically conducting solids, such as sodium-alumina, which has mobile sodium ions.

FIG. 27 is a schematic illustration of an energy storage device 20 which comprises a body 22 optionally filled with electrolyte 24, and an anode 26 and a cathode 28 disposed within body 22. Body 22 can include one or more cell units, each being defined between one anode and one cathode, as known in the art. Device 20 can serve as a battery, in which case anode 26 and cathode 28 form a redox couple, or a supercapacitor, in which case electrical energy is stored electrostatically.

Anode 26 and/or cathode 28 are coated, at least partially, with a solid deposition 32 and 30, respectively. In various exemplary embodiments of the invention a separator 38 is introduced between anode 26 and cathode 28. Separator 38 can be made of a separating material used in typical supercapacitors or batteries. Optionally, electrically conducting contacts 34 and 36 are connected to anode 26 and cathode 28, respectively. The biomolecules in depositions 32 and 30 are preferably selected in accordance with the function of the respective electrode. Due to the aforementioned properties of the solid deposition, anode 28 and/or cathode 28 can pass through very large recharging and discharging electrical current without causing joule heat, nor accompanying heat effects. Therefore, it greatly reduces recharging time.

A substrate coated with a biomolecule by vapor deposition can be used to form a part of a sensor device.

FIG. 28 is a schematic illustration of a sensor device 10, according to various exemplary embodiments of the present invention. Device 10 generally comprises a substrate 12 having a solid deposition 14 of biomolecules thereon. Deposition 14 serves as a sensing component of device 10. The biolmolecules of deposition 14 are selected in accordance with the physical or chemical entity for which sensor 14 is designated. For example, when device 10 is used for sensing a particular molecule, the biomolecules of deposition 14 can be a material which induces an electron transfer upon interacting with the particular molecule. In some embodiments of the present invention deposition 14 serves as a substrate for the attachment of another molecule such as an enzyme, an antibody or the like hence to enact the sensing component of device 10. The surface of deposition 14 can be modified so as to allow the attachment of molecules with specificity to the compound or molecule to be sensed. The biomolecules of deposition 14 can also be light-sensitive so as to allow detection of photons.

Device 10 further comprises two or more electrodes 16 which contact with deposition 14 at one or both sides. In use, a particle, molecule, atom or photon 18 interacts with deposition 14 to generate a signal through electrodes 16.

FIG. 29 is a schematic illustration of another type of sensor device 40, in accordance with some embodiments of the present invention. Device 40 generally comprises a substrate 42 and one or more alignment electrodes 44 attached to or formed on substrate 42. Surface 46 of substrate 42 is preferably electrically isolating, but the bulk of substrate 42 can be made of a semiconductor material. Thus, in various exemplary embodiments of the invention substrate 42 comprises a non-conductive layer 50 and a semiconductor layer 52.

Two solid depositions 48 are deposited on surface 46 on both sides of electrode 44 such that there is a contact between electrodes 44 and depositions 48. The nanostructures forming depositions 48 are preferably electrically conductive. Spaced apart from solid depositions 48 is a gate electrode 54 attached to or formed on surface 46. An electron transfer measurement device 56 coupled to electrodes 44 and 54 measures a quantity indicative of the amount of electrons being transferred along solid depositions 48. Such electron transfer can be towards or away from electrode 44 depending on the type of semiconductor layer 52. Sensor 40 can be used for sensing presence of atoms, molecules or photons interacting with solid deposition 48.

The solid deposition of the present embodiments can also be used to form a coat or pattern of desired property on various of surfaces.

In some embodiments of the present invention the solid deposition has specific fluid contact characteristics. For example, the solid deposition can exhibit a reduced or enhanced friction when contacting a fluid. When the solid deposition exhibits a relatively low fluid friction it has resistant to wetting. Surfaces that are resistant to wetting by fluid are generally termed lyophobic. Specifically, a surface that is resistant to wetting by water is termed "hydrophobic," and a surface that is resistant to wetting by oil is termed oleophobic.

The resistance to wetting can be quantified by the stationary contact angle that a droplet of the fluid forms with the surface. When the contact angle is larger than 90°, the surface is defined as a lyophobic surface or a surface which is resistant to wetting. Thus, a hydrophobic surface is characterized in that the contact angle of a water drop on the surface is larger than 90°, and a oleophobic surface is characterized in that the contact angle of an oil drop on the surface is larger than 90°.

When the contact angle is very large (typically larger than 150°) the surface is defined as a superlyophobic surface or a surface having super-resistance to wetting. A superhydrophobic surface is characterized in that the contact angle of a water drop on the surface is larger than 150°, and a superoleoophobic surface is characterized in that the contact angle of an oil drop on the surface is larger than 150°

In various exemplary embodiments of the invention the solid deposition is characterized by a fluid (e.g., water) contact angle which is larger than 90°, more preferably larger than 120°, more preferably larger than 130°, more preferably larger than 140°, more preferably larger than 150°, e.g., about 160°.

In some embodiments, the solid deposition is characterized in that upon impact of liquid drops on the solid deposition, the drops are bounced off the solid deposition. Such bouncing effect is advantageous in many applications, including, without limitation high-accuracy activation or passivation of substrates by microdrops, transport of surface contaminants into bulk liquids, gas entrapment ink-jet printing, rapid spray cooling of hot surfaces, direct jet impingement for power electronics cooling, quenching, etc.

In some embodiments of the present invention the solid deposition is used as a hydrophobic or superhydrophobic coat or pattern. Preferably, such hydrophobic coat or pattern is characterized in that a liquid has a contact angle of from about 120° to about 180° on the coat or pattern. It was found by the Inventors of the present invention that when the solid deposition is made of nanostructures which are aligned generally perpendicular to the substrate.

Coats or patterns with hydrophobic properties can be used according to some embodiments of the present invention in many applications, including, without limitation microfluidic devices, self-cleaning surfaces and the like.

For microfluidic devices, the solid deposition of the present embodiments is preferably applied in patterns so as to form fluid channels on a substrate.

FIGS. 34a-b are schematic illustrations of a microfluidic device 60, according to various exemplary embodiments of the present invention. FIG. 34a is a perspective view and FIG. 34b is a cross sectional view along line A-A. Device 60 generally comprises a device body 62 with one or more flow channels 64 deposited thereon. Body 62 may comprise one or more substrate 66. In the representative illustration in FIGS. 34a-b body 62 includes two parallel planar substrates a main substrate 66a and a cover substrate 66b. However, this need not necessarily be the case, since, for some applications, it may not be necessary for body 62 to have two substrates. For example, device 60 can include only main substrate 66a and be devoid of a cover substrate. Further, although the substrates are shown planar in FIGS. 34a-b, this need not necessarily be the case; substrate 66 is not necessarily planar.

Channel(s) 64 are preferably formed by vapor deposition of patterns of biomolecules to form a solid deposition 68 on substrate 66a as further detailed hereinabove. In some embodiments, solid deposition 68 is hydrophobic such that channel(s) 64 are defined in areas on substrate 66a which are devoid of solid deposition 68. In this embodiment, channel(s) 64 are defined in the lateral dimension (parallel to substrate 66a) "walls" 70 of solid deposition 68, and in the vertical dimension (perpendicular to substrate 66a) by substrate 66a and optionally substrate 66b. Also contemplated is an embodiment in which channel(s) 64 are in the form of recesses in substrate 66a. This embodiment can be combined with hydrophobic solid deposition 68 wherein walls 70 are arranged sidewise with the recesses.

In various exemplary embodiments of the invention the solid deposition of biomolecules has a nanometric pattern. In some embodiments the solid deposition comprises nanostructures as described above. To enhance the hydrophobic property of the deposition, the nanostructures can be arranged generally perpendicularly to substrate 66a.

Any number of channels is contemplated. In the exemplified illustration of FIG. 34a, channel(s) 64 includes a primary channel which is in fluid communication with a plurality of secondary channels via one or more branching points 72. The primary channel can be a linear channel or it can have linear parts and nonlinear parts. Other configurations for the channels are also contemplated. When there is more than one branching point each branching point is preferably located such as to allow fluid to furcate upon arrival the branching point.

A fluid medium can be fed into device 60 via one or more inlet ports 74. The fluid medium can be delivered to ports 74 by a fluid supply unit (not shown) which can be or comprise a flow rate controller to ensure a predetermined flow rate to inlet port 74. The fluid medium particles can be evacuated from device 60 through one or more outlet ports 76.

In some embodiments of the present invention, a microfluidic device comprising fluid channels formed as patterned solid deposition is a part of an integrated device, such as an integrated separation or detection equipment or an integrated circuit. Fluids used in the microfluidic device of the present embodiments include, without limitation, water, whole blood samples, bacterial cell suspensions, protein or antibody solutions and various buffers and saline.

Applications for the microfluidic device of the present embodiments include, without limitation, genetic, chemical, biochemical, pharmaceutical, biomedical, chromatography, integrated circuit cooling, ink-jet printing, medical, radiological and environmental applications. The medical applications include without limitation, diagnostic and patient management such as implanted drug dispensing systems. The environmental applications include, without limitation, detecting hazardous materials or conditions such as air or water pollutants, chemical agents, biological organisms or radiological conditions. The genetic and biochemical applications include, without limitation, testing and/or analysis of DNA, and other macro or smaller molecules, or reactions between such molecules in microfluidic device 60, in an approach known as "lab-on-chip."

The microfluidic device of the present embodiments can also be used in chemical and biochemical sensing, molecular separations, drug delivery and other forefront technologies. In a manner similar to that for microelectronics, the microfluidic device of the present embodiments enables the fabrication of highly integrated devices applicable to high throughput, low volume, automatable chemical and biochemical analyses and syntheses. Fluids which can be used in the microfluidic device of the present embodiments include water, whole blood samples, bacterial cell suspensions, protein or antibody or nucleic acid solutions and various buffers.

The microfluidic device of the present embodiments can be used to obtain a variety of measurements including, without limitation, molecular diffusion coefficients, fluid viscosity, pH, chemical binding coefficients and enzyme reaction kinetics. Also contemplated are other applications, including, without limitation, capillary electrophoresis, isoelectric focusing, immunoassays, flow cytometry, sample injection of proteins for analysis via mass spectrometry, sample injection of air or water samples for analysis via flamespectrometry, polymerase chain reaction (PCR) amplification, DNA analysis, cell manipulation, cell separation, cell patterning and chemical gradient formation.

For self-cleaning surfaces, the solid deposition of the present embodiments is preferably applied to coat the entire surface, substantially uniformly. In this embodiment, the biomolecules of the solid deposition can be selected such as to provide large contact angle. In various exemplary embodiments of the invention the solid deposition of biomolecules has a nanometric pattern. In some embodiments the solid deposition comprises nanostructures as described above. To enhance the hydrophobic property of the deposition, the nanostructures can be arranged generally perpendicularly to the substrate. Optionally and preferably, the biomolecules of the solid deposition are additionally selected so as to ensure low sliding or rolling angle of liquid on the substrate. The sliding or rolling angle is defined as the angle at which the surface must be tilted to cause sliding or rolling of a liquid drop.

The substrate and/or biomolecules of the solid deposition of the present embodiments can be transmissive, reflective or adsorptive to any type of electromagnetic radiation. It was found by the Inventors of the present invention that the transmittance of the solid deposition to electromagnetic radiation, particularly, but not exclusively, visible light, can be controlled by a judicious selection of the thickness of the solid deposition. Specifically, higher transmittance can be achieved by fabricating a solid deposition of lower thickness (typically, but not obligatorily, few micrometers or less), and lower transmittance can be achieved by fabricating a solid deposition of higher thickness (typically, but not obligatorily, 10 micrometers or more).

In some embodiments of the present invention the substrate and biomolecules are transmissive to visible light. For example, a light-transmissive hydrophobic solid deposition of biomolecules can coat in accordance with some embodiments of the present invention a window glass, solar cell panels, glassware, lenses and the like to form a self-cleaning transparent object.

In some embodiments, Another example, a light-reflective solid deposition of biomolecules can coat black mirrors used in solar cell devices.

It is expected that during the life of a patent maturing from this application many relevant compositions-of matter having a substrate coated with a biomolecule by vapor deposition will be developed and the scope of the phrase "a substrate coated with a biomolecule by vapor deposition" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Materials and Methods

All the biomolecules used in the following experiments, such as amino acids phenylalanine (F), tryptophan (W), tyrosine (Y), natural and non-natural peptides, diphenylalanine (FF), triphenylalanine (FFF), N-tert-butoxycarbonyl-diphenylalanine (Boc-FF), 9-fluorenylmethylcarbonyl-pentafluorophenylalanine (Fmoc-F5-F), 9-fluorenylmethylcarbonyl-dipentafluorophenylalanine (Fmoc-F5-FF), 9-fluorenylmethylcarbonyl-diphenylalanine (Fmoc-FF), dityrosine (YY), dialanine (AA), diglycine (GG), 3,4-dihydroxy-phenylalanine (DOPA), poly-phenylalanine (Poly-F), arginine-glycine-aspartic acid (RGD), bovine serum albumin (BSA) and other biomolecules such as adenosine triphosphate (ATP) and adenine (A), were obtained from Sigma Israel, Bachem Switzerland or synthesized in the laboratory.

All other chemicals, such as fluorescein (FLU) and calcein (CALC), were obtained from Sigma Israel unless stated otherwise.

Vapor deposition equipment was partly fabricated and assembled in-house.

Deep vacuum was achieved using a turbo-molecular pump system by Pfeiffer, Germany.

Morphology and topography features of the deposited biofilms were studied by conventional scanning electron microscopy (SEM) by Jeol, Germany. Additionally, the samples with biofilms were imaged by an optical microscope by Olympus, USA, and atomic force microscopy (AFM) by Multimode, Digital Instruments, USA.

Time-of-flight secondary-ion mass spectrometry (ToF-SIMS) analysis was used to characterize the chemical structure and composition of elements contained on the coated surface using a Physical Electronics TRIFT II ToF-SIMS instrument.

Example 1

Uniform Coating of Flat Solid Surfaces

Biomolecules vapor deposition method was performed on solid substrates of various origins such as metal Ti-alloy, Au, Ag, Cu, Ni, Si, glass, amorphous $SiO_2$, amorphous $Si_3N_4$, hydroxyapatite ceramics (HAp) and related calcium phosphates, graphite and carbon samples, and ferroelectric crystals such as $LiNbO_3$. The substrates used for the biomolecules deposition were cleaned by standard cleaning methods using acetone and isopropanol solutions.

The apparatus used to effect the vapor deposition according to some embodiments of the present invention is shown in FIG. 1 as discussed hereinabove.

Coating of Various Substances with a Film of Diphenylalanine:

A powder of diphenylalanine FF (5 mg) was placed on the sample holder (see sample holder 7 in FIG. 1). The solid substrates of various origins were placed on the substrate holder (see substrate holder 4 in FIG. 1). The chamber was closed and sealed, and subsequently the turbo-molecular pump was operated to bring the vacuum to a stable level of $10^{-6}$ Torr. Thereafter the heating unit (see, heating/cooling unit 3 in FIG. 1) was operated using the control unit (see, control unit 9 in FIG. 1) and was heated to 230° C. for a duration of 0.5 minutes. Thereafter the heating was ceased and the system was allowed cooled to room temperature. The substrate coated by a homogeneous layer of FF, was removed from the chamber and inspected visually and microscopically.

FIG. 2 presents images of a glass substrate having a film of diphenylalanine (FF) deposited thereon using optimal vapor deposition conditions and system parameters as presented and described hereinabove, wherein FIG. 2A shows the glass surface at a low magnification of an optical microscope and FIG. 2B is a high magnification SEM micrograph showing the FF film on the glass surface. As can be seen in FIG. 2A, a uniform and homogeneous distribution of FF was observed over all the substrate exposed area. FIG. 2B reveals the microstructure of the deposited thin FF film, showing the needle-like features formed by the deposited FF.

A time-of-flight secondary-ion mass spectrometry (ToF-SIMS) analysis was applied to characterize the chemical structure and composition of elements contained on the film-coated glass surface. FIG. 3 presents a ToF-SIMS spectrum obtained from the deposited film of FF using a 15 kV primary ion gun, showing the positive ions fingerprint of the vapor deposited FF. As can be seen in FIG. 3, a peak at about 295 m/z, characteristic to FF, was found in the positive ion spectrum, indicating the presence of FF molecules in the deposited film. It should be mentioned that no impurities were observed in both positive and negative ToF-SIMS spectra obtained from vapor deposited FF films.

FIG. 4 presents optical micrographs of the surfaces of different substrates onto which FF was deposited using vapor deposition, such as silicon dioxide (silica, $SiO_2$, FIG. 4A), hydroxylapatite ($Ca_5(PO_4)_3(OH)$, HAp) ceramics (FIG. 4B before deposition and FIG. 4C after deposition), and titanium (Ti, FIG. 4D before deposition and FIG. 4E after deposition). As can be seen in FIGS. 4A, 4C and 4E, a uniform and homogeneous distribution of FF was observed on all the substrates over all the exposed area.

Coating of Glass with a Film of Various N-Protected Diphenylalanine:

FIG. 5 presents images of a glass substrate having a film of N-tert-butoxycarbonyl-diphenylalanine (Boc-FF) deposited thereon using optimal vapor deposition conditions and system parameters as presented and described hereinabove. The chamber was operated at vacuum pressure of $10^{-6}$ Torr. Once the vacuum was stable, the heating unit (see, heating/cooling unit 3 in FIG. 1) was operated using the control unit (see, control unit 9 in FIG. 1) and was heated to 180° C. for a duration of 0.5 minutes. Thereafter the heating was ceased and the system was allowed cooled to room temperature. The substrate coated by a homogeneous layer of Boc-FF, was removed from the chamber and inspected visually and microscopically.

FIG. 6 presents images of a glass substrate having a film of 9-fluorenylmethylcarbonyl-diphenylalanine (Fmoc-FF) deposited thereon using optimal vapor deposition conditions and system parameters as presented and described hereinabove, set to a vacuum pressure of $10^{-6}$ Torr and heating temperature of 210° C. for a duration of 0.5 minutes. The substrate coated by a homogeneous layer of Fmoc-FF, was removed from the chamber and inspected visually and microscopically.

As can be seen in FIGS. 5 and 6, a uniform and homogeneous distribution of Boc-FF and Fmoc-FF respectively was observed over all the substrate exposed area.

Coating of Glass with a Film of Dityrosine:

FIG. 7 presents images of a glass substrate having a film of dityrosine (YY) deposited thereon using optimal vapor deposition conditions and system parameters as presented and described hereinabove, set to a vacuum pressure of $10^{-6}$ Torr and heating temperature of 230° C. for a duration of 0.5 minutes. The substrate coated by a homogeneous layer of YY, was removed from the chamber and inspected visually and microscopically.

FIG. 7A shows the glass surface at a low magnification of an optical microscope and FIG. 7B is a high magnification SEM micrograph showing the YY-coated glass surface. As can be seen in FIG. 7A, a uniform and homogeneous distribution of YY was observed over all the substrate area. FIG. 7B reveals the microstructure of the deposited thin YY film, showing the fine features formed by the deposited YY.

Coating of Glass with a Film of Dialanine:

FIG. 8 presents images of a glass substrate having a film of dialanine (AA) deposited thereon using optimal vapor deposition conditions and system parameters as presented and described hereinabove, set to a vacuum pressure of $10^{-6}$ Torr and heating temperature of 200° C. for a duration of 0.5 minutes. The substrate coated by a homogeneous layer of AA, was removed from the chamber and inspected visually and microscopically.

FIG. 8A shows the glass surface at a low magnification of an optical microscope and FIG. 8B is a high magnification SEM micrograph showing the FF-coated glass surface. As can be seen in FIG. 8A, a uniform and homogeneous distribution of AA was observed over all the substrate exposed area. FIG. 8B reveals the microstructure of the deposited thin AA film, showing the urchin-like features formed by the deposited AA. It is noted herein that AA was also deposited on different substrates, such as Si-semiconductor crystal, amorphous dielectric $SiO_2$, Ti-metal alloy and ferroelectric crystals $LiNbO_3$ with similar results.

Coating of Glass with a Film of Diglycine:

FIG. 9 presents a low magnification optical micrograph of a glass substrate having a film of diglycine (GG) deposited thereon using optimal vapor deposition conditions and system parameters as presented and described hereinabove, set to a vacuum pressure of $10^{-6}$ Torr and heating temperature of 220° C. for a duration of 0.5 minutes. The substrate coated by a homogeneous layer of GG, was removed from the chamber and inspected visually and microscopically.

As can be seen in FIG. 9, a uniform and homogeneous distribution of GG was observed over all the substrate exposed area. It is noted herein that GG was also deposited on different substrates with similar results.

Coating of Silica with a Film of Phenylalanine:

FIG. 10 presents images of a silica substrate having a film of phenylalanine (F) deposited thereon using optimal vapor deposition conditions and system parameters as presented and described hereinabove, set to a vacuum pressure of $10^{-6}$ Torr and heating temperature of 210° C. for a duration of 0.5 minutes. The substrate coated by a homogeneous layer of F, was removed from the chamber and inspected visually and microscopically.

FIG. 10A shows the silica surface at a low magnification of an optical microscope and FIG. 10B is a high magnification SEM micrograph showing the F-coated silica surface. As can be seen in FIG. 10A, a uniform and homogeneous distribution of F was observed over all the substrate exposed area. FIG. 10B reveals the microstructure of the deposited thin F film, showing the blob-like features formed by the deposited F. It is noted herein that F was also deposited on different substrates with similar results.

Coating of Silicon and Glass with a Film of 3,4-dihydroxyphenylalanine:

FIG. 11 presents images of silicon and glass substrates having a film of 3,4-dihydroxyphenylalanine (DOPA) deposited thereon using optimal vapor deposition conditions and system parameters as presented and described hereinabove, set to a vacuum pressure of $10^{-6}$ Torr and heating temperature of 250° C. for a duration of 0.5 minutes. The substrate coated by a homogeneous layer of DOPA, was removed from the chamber and inspected visually and microscopically.

FIGS. 11A and 11B show optical micrographs of silicon and glass respectively, and FIG. 11C is a high magnification SEM micrograph showing the DOPA-coated glass surface. As can be seen in FIGS. 11A and 11B, a uniform and homogeneous distribution of DOPA was observed over all the substrate exposed area. FIG. 11C reveals the microstructure of the deposited thin DOPA film, showing the blob-like features formed by the deposited DOPA. It is noted herein that DOPA was also deposited on different substrates with similar results.

Coating of Silicon and Glass with a Film of Tryptophan:

FIG. 12 presents images of silicon and glass substrates having a film of tryptophan (W) deposited thereon using optimal vapor deposition conditions and system parameters as presented and described hereinabove, set to a vacuum pressure of $10^{-6}$ Torr and heating temperature of 200° C. for a duration of 0.5 minutes. The substrate coated by a homogeneous layer of W, was removed from the chamber and inspected visually and microscopically.

FIGS. 12A and 12B show optical micrographs of glass and silicon respectively, and FIG. 12C is a high magnification SEM micrograph showing the W-coated glass surface. As can be seen in FIGS. 12A and 12B, a uniform and homogeneous distribution of W was observed over all the substrate exposed area. FIG. 12C reveals the microstructure of the deposited thin W film, showing the flake-like features formed by the deposited W. It is noted herein that W was also deposited on different substrates with similar results.

Coating of Silicon and Glass with a Film of Tyrosine:

FIG. 13 presents images of silicon and glass substrates having a film of tyrosine (Y) deposited thereon using optimal vapor deposition conditions and system parameters as presented and described hereinabove, set to a vacuum pressure of $10^{-6}$ Torr and heating temperature of 150° C. for a duration of 0.5 minutes. The substrate coated by a homogeneous layer of Y, was removed from the chamber and inspected visually and microscopically.

FIGS. 13A and 13B show optical micrographs of glass and silicon respectively, and FIG. 13C is a high magnification SEM micrograph showing the Y-coated silicon surface. As can be seen in FIGS. 13A and 13B, a uniform and homogeneous distribution of Y was observed over all the substrate exposed area. FIG. 13C reveals the microstructure of the deposited thin Y film, showing the needle-like features formed by the deposited Y. It is noted herein that Y was also deposited on different substrates with similar results.

Coating of Glass with a Film of Triphenylalanine:

FIG. 14 presents a low magnification optical micrograph of a glass substrate having a film of triphenylalanine (FFF) deposited thereon using optimal vapor deposition conditions and system parameters as presented and described hereinabove, set to a vacuum pressure of $10^{-6}$ Torr and heating temperature of 190° C. for a duration of 0.5 minutes. The substrate coated by a homogeneous layer of FFF, was removed from the chamber and inspected visually and microscopically.

As can be seen in FIG. 14 a uniform and homogeneous distribution of FFF was observed over all the substrate exposed area.

Coating of $Si_3N_4$ with a Film of Fmoc-F5-F:

A film of 9-fluorenylmethylcarbonyl-pentafluorophenylalanine (Fmoc-F5-F) was deposited on a $Si_3N_4$ substrate using optimal vapor deposition conditions and system parameters as presented and described hereinabove.

The chamber was operated at vacuum pressure of $10^{-6}$ Torr. Once the vacuum was stable, the heating unit (see, heating/cooling unit 3 in FIG. 1) was operated using the control unit (see, control unit 9 in FIG. 1) and was heated to 100° C. for a duration of 0.5 minutes. Thereafter the heating was ceased and the system was allowed cooled to room temperature. The substrate coated by a homogeneous layer of F5-F was removed from the chamber and inspected.

FIG. 25 are optical and SEM images of an $Si_3N_4$ substrate having a film of Fmoc-F5-F deposited thereon. A uniform and homogeneous distribution of the Fmoc-F5-F material was observed all over the deposition area.

Coating of Glass with a Film of Fmoc-F5-FF:

A film of 9-fluorenylmethylcarbonyl-dipentafluorophenylalanine (Fmoc-F5-FF) was deposited on a glass substrate using optimal vapor deposition conditions and system parameters as presented and described hereinabove.

The chamber was operated at vacuum pressure of $10^{-6}$ Torr. Once the vacuum was stable, the heating unit (see, heating/cooling unit 3 in FIG. 1) was operated using the control unit (see, control unit 9 in FIG. 1) and was heated to 170° C. for a duration of 0.5 minutes. Thereafter the heating was ceased and the system was allowed cooled to room temperature. The substrate coated by a layer of Fmoc-F5-FF was removed from the chamber and inspected.

FIG. 26 is an optical image of a glass substrate having a film of Fmoc-F5-FF deposited thereon. A uniform and homogeneous distribution of the Fmoc-F5-FF material was observed all over the deposition area.

Coating of Glass with a Film of RGD:

RGD, which is the one-letter amino acid code abbreviation for the tripeptide arginine-glycine-aspartic acid, is part of the recognition sequence for integrin binding to many extracellular matrix proteins, and one of the most studied peptides in pharmacology and drug development research.

FIG. 15 presents a low magnification optical micrograph of a glass substrate having a film of arginine-glycine-aspartic acid (RGD) deposited thereon using optimal vapor deposition conditions and system parameters as presented and described hereinabove, set to a vacuum pressure of $10^{-6}$ Torr and heating temperature of 180° C. for a duration of 0.5 minutes. The substrate coated by a homogeneous layer of RGD, was removed from the chamber and inspected visually and microscopically.

As can be seen in FIG. 15, a uniform and homogeneous distribution of RGD was observed over all the substrate exposed area.

Coating of Glass with a Film of Polyphenylalanine:

The poly-phenylalanine sample contained polypeptide molecules at a molecular weight distribution of 5,000-15,000 Daltons.

FIG. 16 presents a low magnification optical micrograph of a glass substrate having a film of polyphenylalanine (Poly-F) deposited thereon using optimal vapor deposition conditions and system parameters as presented and described hereinabove, set to a vacuum pressure of $10^{-6}$ Torr and heating temperature of 230° C. for a duration of 0.5 minutes. The substrate coated by a homogeneous layer of Poly-F was removed from the chamber and inspected visually and microscopically.

As can be seen in FIG. 16, a film of Poly-F with interlacing ribs thereof was observed over all the substrate exposed area. It is noted herein that Poly-F was also deposited on different substrates with similar results.

Coating of Glass with a Film of Bovine Serum Slbumin:

Bovine serum albumin (BSA) is a 583 residue long protein having a molecular weight of 66.430 kDa.

FIG. 17 presents a low magnification optical micrograph of a glass substrate having a film of BSA deposited thereon using optimal vapor deposition conditions and system parameters as presented and described hereinabove, set to a vacuum pressure of $10^{-6}$ Torr and heating temperature of 200° C. for a duration of 0.5 minutes. The substrate coated by a homogeneous layer of BSA was removed from the chamber and inspected visually and microscopically.

As can be seen in FIG. 17, a film of BSA was observed over all the substrate exposed area.

Coating of Silica with a Film of Various Fluorescent Agents:

Fluorescein (FLU), also known as resorcinolphthalein, is a fluorogenic detectable agent which is used in chromatography, for highlighting and contrasting imaging and microscopy, as a type of dye laser as the gain medium, in forensics and serology to detect latent blood stains, and in various dye tracing techniques.

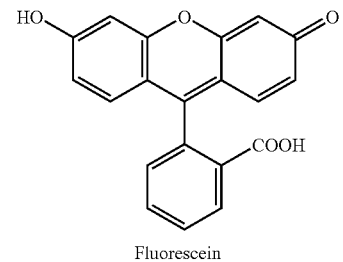 [SMILES: O=C(O)c1ccccc1-c1c2ccc(=O)cc-2oc2cc(O)ccc12]

Fluorescein

FIG. 18 presents a low magnification optical micrograph of a glass substrate having a film of FLU deposited thereon using optimal vapor deposition conditions and system parameters as presented and described hereinabove, set to a vacuum pressure of $10^{-6}$ Torr and heating temperature of 200° C. for a duration of 0.5 minutes. The substrate coated by a homogeneous layer of FLU was removed from the chamber and inspected visually and microscopically.

Calcein (CALC), also known as fluorexon, is a derivative of fluorescein which is used as a complexometric indicator for titration of calcium ions with EDTA, and for fluorometric determination of calcium.

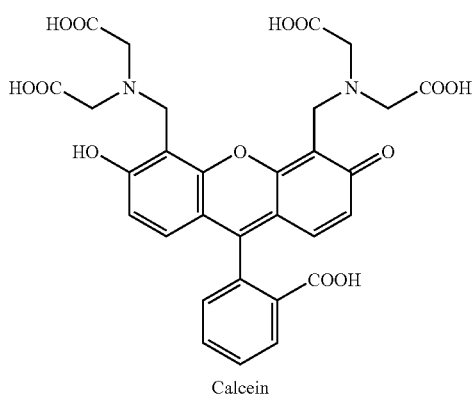 [SMILES: O=C(O)CN(CC(=O)O)Cc1c2oc3c(CN(CC(=O)O)CC(=O)O)c(O)ccc3c(-c3ccccc3C(=O)O)c-2ccc1=O]

Calcein

FIG. 19 presents a low magnification optical micrograph of a glass substrate having a film of CALC deposited thereon using optimal vapor deposition conditions and system parameters as presented and described hereinabove, set to a vacuum pressure of $10^{-6}$ Torr and heating temperature of 200° C. for a duration of 0.5 minutes. The substrate coated by a homogeneous layer of CALC was removed from the chamber and inspected visually and microscopically.

As can be seen in FIGS. 18 and 19, a uniform and homogeneous distribution of FLU and CALC respectively was observed over all the substrate exposed area.

Film Thickness, Distribution and Morphology Adjustment:

In all the above experiments, the thickness and distribution of the deposited biomolecules was controlled by adjusting the condition and parameters of the vapor deposition process.

FIG. 20 presents AFM micrographs of FF-coated glass surfaces, showing the variation in homogeneity and morphology, and the variations in thickness of the deposited biomolecule layer as measured by AFM tapping mode, wherein FIGS. 20A, 20B and 20C show the FF layer of 50 nm, 1.7 μm and 2.9 μm respectively, obtained at a vacuum pressure of $10^{-6}$ Torr and a sample heating temperature of 150° C., 200° C. and 230° C. for a duration of 0.5 minutes each.

As can be seen in FIG. 20, the thickness of the diphenylalanine (FF) coat, deposited on glass surfaces, which was measured using atomic-force microscopy in tapping mode, varied from 50 nm (FIG. 20A) to 1.7 μm (FIG. 20B) to 2.9 μm (FIG. 20C) according to the temperature, pressure and duration of the vapor deposition process.

Biomolecules may self-assemble into rods, needles, spheroids, tubes, wires, fibers, nanotubes, tapes, films, flakes and other nanostructures during the vapor deposition process, depending on the conditions of the deposition process.

FIG. 21 presents SEM micrographs of FF- and DOPA-coated silicon surfaces, showing the variation in morphology of the deposited biomolecule layer, wherein FIG. 21A shows an FF layer of nanotubes obtained at a vacuum pressure of $10^{-6}$ Torr and a sample heating temperature of 220° C. for a duration of 0.5 minutes, and FIG. 21B shows a DOPA film of interconnected blobs obtained at a vacuum pressure of $10^{-6}$ Torr and a sample heating temperature of 250° C. for a duration of 0.5 minutes.

Thin film of biomolecules may be achieved by controlling the adhesion of the deposited biomolecules to the substrate. In such a way the adhesion force of deposited biomolecules may be varied controllably either homogenously or in selected locations of the substrate.

FIG. 22 presents SEM micrographs of a bio-tape, or a free standing film, achieved by physical removing the vapor-deposited F biomolecule layer from a silica substrate with preliminary modified adhesion properties, in order to obtain a low adhesion of deposited F layer on silica substrate. Low adhesion was achieved using the technique described in International Publication No. WO 2007/049380, to G. Rosenman, D. Aronov and Yu. Dekhtyar, the contents of which are hereby incorporated by reference. The chamber was operated at vacuum pressure of $10^{-6}$ Torr. Once the vacuum was stable, the heating unit was operated using the control unit and was heated to 210° C. for a duration of 0.5 minutes. Thereafter the heating was ceased and the system was allowed cooled to room temperature. The substrate coated by a homogeneous layer of F, was removed from the chamber and the deposited layer of F biomolecules was separated from the silica substrate by means of physical removing. FIG. 22A shows a front view of the film and FIG. 22B shows a side view of the thin film of F as afforded according to the above procedure.

Example 2

Patterned Coating of Flat Solid Surfaces

Substrates with patterned coating of biomolecules were obtained using particular variations of the deposition process parameters. One exemplary variation involved vapor deposition of biomolecules through a shadow mask or a patterned physical mask deposited on the surface of the substrate.

FIG. 23 presents a SEM micrograph of a glass substrate having a micro-pattered FF coat obtained by using a shadow mask of silicon with 100 μm diameter holes that was physically attached to the glass substrate. The chamber was operated at vacuum pressure of $10^{-6}$ Torr. Once the vacuum was stable, the heating unit was operated using the control unit and was heated to 230° C. for a duration of 0.5 minutes. Thereafter the heating was ceased and the system was allowed cooled to room temperature. The substrate coated through the shadow mask with formed patterned layer of FF was removed from the chamber and inspected visually and microscopically.

As can be seen in FIG. 23, urchin-like nodes of FF, arranged in an array of distinct addressable locations following the hard silicon mask of arrayed holes, were observed over all the exposed area of the substrate.

Another way to obtain patterned coating of biomolecules at a micro-nano-resolution on a substrate can be afforded by subjecting a pre-fabricated homogeneous coating film to selective spatially-patterned irradiation of electrons (ions) or light, or the application of other methods of micro-nano-lithography. Patterning may be effected in 1-, 2- and 3-dimensions, affording various shapes using aforementioned methods.

FIG. 24 presents a SEM micrograph of a micro-patterned FF film on a glass substrate using non-filtered Hg—Xe lamp light (200 W Hg—Xe lamp by Hamamatsu, Japan) shone through a silicon shadow mask having 100 μm diameter holes that was attached to the glass substrate. Preliminary, the homogeneous layer of FF biomolecules was obtained as described hereinabove. Thereafter, the homogeneously coated by FF biomolecules glass sample was illuminated by Hg—Xe lamp light for 3 minutes through the aforementioned silicon shadow mask with 100 μm diameter holes that was physically attached to the coated substrate. Hg—Xe lamp light illumination resulted in the decomposition of the FF biomolecule and as a result, micro-patterning of the FF film was obtained directly on the glass substrate. Similar results can be afforded by local heating of the preliminary deposited FF layer, resulting in localized and patterned decomposition of the FF biomolecule.

As can be seen in FIG. 24, the layer of FF, which covered the entire exposed area of the substrate prior to the Hg—Xe lamp illumination, was punctured by holes arranged in an array of distinct addressable locations following the shadow silicon mask of arrayed holes, were observed. Similar patterning may be achieved using any lithography technique known in the art.

Example 3

Hydrophobic Coating and Patterning

Figure 30A:
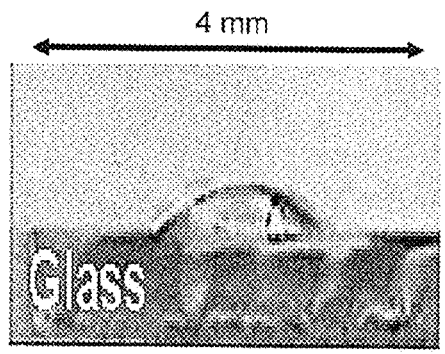
Figure 30B:
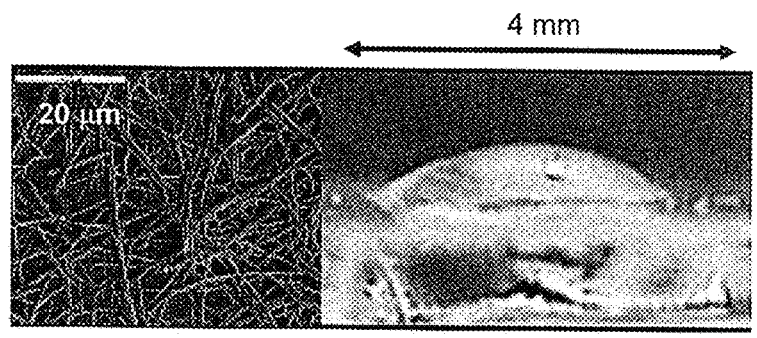
Figure 30C:
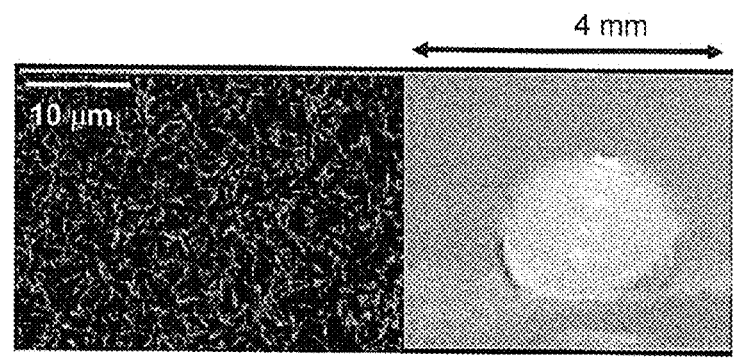

FIGS. 30a-d are images demonstrating the ability of the solid deposition of the present embodiments to form a hydrophobic coat on a substrate. FIG. 30a shows a drop of water on a glass substrate, in which the contact angle is about 25°. FIG. 30b shows a drop of water on horizontally aligned diphenylalanine nanostructures deposited by vapor deposition on a glass substrate, in which the contact angle is about 30°. FIG. 30c shows a drop of water on vertically aligned diphenylalanine nanostructures deposited by vapor deposition on a glass substrate, in which the contact angle is about 135°.

The present embodiments also contemplate forming a superhydrophobic surface which is characterized by a contact angle which is larger than 150°.

Figure 30D:
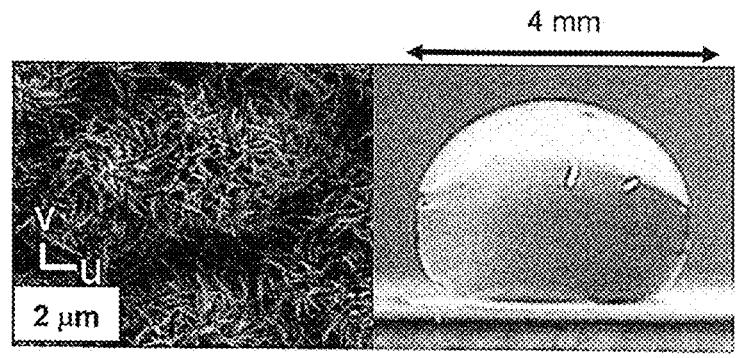

FIG. 30d shows a drop of water on a solid deposition of Fmoc-F5-FF nanostructures deposited by vapor deposition on a glass substrate. The measured contact angle was about 160°. An effect of bouncing drops was observed upon impact of liquid drops on the solid deposition. FIG. 32 shows snapshots of a millimeter-size water droplet before, during, and after initial impact with an Fmoc-F5-FF. The snapshots were taken and are displayed over a period of 1 second. As demonstrated, the water drop is fully rebounded from the Fmoc-F5-FF coat.

FIG. 31 demonstrates the ability of the solid deposition of the present embodiments to form a hydrophobic pattern. Shown in FIG. 31 are two exemplary hydrophobic patterns of diphenylalanine deposited by vapor deposition on a $SiO_2$ substrate. The dark regions in FIG. 31 correspond to areas which are covered by water. Such patterns can form microfluidic channels or circuits in a microfluidic device.

Example 4

Electrochemical Cell

A cyclic voltammetry experiment was performed using an electrochemical cell having electrodes coated by vapor deposition, according to some embodiments of the present invention.

A graphite working electrode and a graphite counter electrode were coated by vapor deposition to form a 5 m thick solid deposition of FF on the electrodes. The solid deposition included elongated nanostructures which were generally perpendicular to the electrode surface. A representative example of a coated surface of a graphite electrode is shown in FIG. 33a.

The electrochemical cell included the two coated electrode, a reference electrode and electrolyte. The reference electrode was made of Ag/AgCl and the electrolyte was 0.1M NaCl. An additional electrochemical cell in which the working and counter electrodes were not coated (all other elements the same) was also prepared for comparison. A potential difference was applied to the cells and the the redox current density (faradaic current) was measured over a potential window of [−1.5 v, 0] and vice versa.

FIG. 33b is a graph showing the cyclic voltammetry measurements without coating (blue color graph) and with coating (red color graph). As shown, the redox current density with coating is about 10 times higher that the redox current density without coating.

Example 5

Transparent Substrates

Optical transmittance measurements of glass substrates deposited with a solid deposition in accordance with some embodiments of the present invention were performed.

Materials and Methods

Glass substrates were coated with films of FF via vapor deposition as described above. Films with film thicknesses ranging from about 1 m to about 10 µm were fabricated.

Visible light beams of various wavelengths ranging from 400 nm to about 700 nm were directed normally to the coated surfaces.

For comparison raw (uncoated) glass substrates were also provided and illuminated normally thereto.

Results

FIG. 35 is a graph showing the transparency in percentage as a function of the wavelength in nanometers of an uncoated glass (designated "pure" in FIG. 35), a glass coated with a 1-m film of FF (designated "thin" in FIG. 35), and a glass coated with a 10-m film of FF (designated "thick" in FIG. 35). The transparency values were normalized by taking into consideration a level of measured intensity of light in the dark room.

As shown, a glass coated by a 1-m film of FF has approximately the same transparency as a pure glass for all wavelengths in the range 400-700 nm. A glass coated by a 10-m film of FF, on the other hand, is generally nontransparent for wavelengths of from about 400 nm to about 580 nm, and a reduced transparency (less than 70%) for wavelengths of from about 580 nm to about 700 nm. Thus, while a relatively thick film of FF adsorbs or reflects most of the incident light, a relatively thin film is substantially transparent.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A coating method, comprising:
    placing a substrate and a biomolecule that self-assemble in a chamber, said biomolecule is a homodipeptide; and applying a vapor deposition process within said chamber so as to form a solid deposition of said biomolecule on at least a portion of a surface of said substrate.

2. The method of claim 1, wherein at least one of said substrate and said biomolecule is selected such that said biomolecule is self-assembled into nanostructures within said chamber during said vapor deposition process.

3. The method of claim 1, further comprising prior to said application of said vapor deposition process, placing a mask on said surface such that said solid deposition is formed at a predetermined pattern which comprises a plurality of distinct addressable locations.

4. The method of claim 1, further comprising subsequently to said application of said vapor deposition process placing a mask having a predetermined pattern which comprises a plurality of distinct addressable locations on said solid deposition, and irradiating said mask and said solid deposition such that said solid deposition is substantially degraded according to said pattern.

5. The method of claim 2, wherein said nanostructures are responsive to a force field and the method further comprising applying a force field during or subsequently to said application of said vapor deposition process so as to align said nanostructures generally parallel to each other.

6. The method of claim 2, further comprising placing in said chamber a material which is responsive to a force field, and applying a force field during or subsequently to said application of said vapor deposition process so as to align said nanostructures generally parallel to each other.

7. The method of claim 1, further comprising detaching said solid deposition from said surface, thereby obtaining an article-of-manufacture.

8. The method of claim 3 wherein a gap between any two adjacent locations of said plurality of locations ranges is at least 100 nm.

9. The method of claim 1, wherein said vapor deposition process is a physical vapor deposition process.

10. The method of claim 1, wherein said solid deposition is characterized by a thickness ranging from about 100 nm to about 10 μm.

11. The method according to claim 1, wherein said homodipeptide is an aromatic peptide.

* * * * *